(12) United States Patent
Cheng

(10) Patent No.: US 10,799,665 B2
(45) Date of Patent: Oct. 13, 2020

(54) SYSTEM FOR TRACKING MOTION OF A DEVICE

(71) Applicant: PAUSEABLE APS, Ballerup (DK)

(72) Inventor: Peng Cheng, Vaerlose (DK)

(73) Assignee: PAUSEABLE APS, Ballerup (DK)

( * ) Notice: Subject to any disclaimer, the term of this patent is extended or adjusted under 35 U.S.C. 154(b) by 320 days.

(21) Appl. No.: 15/548,397

(22) PCT Filed: Feb. 5, 2016

(86) PCT No.: PCT/EP2016/052509
§ 371 (c)(1),
(2) Date: Aug. 2, 2017

(87) PCT Pub. No.: WO2016/124742
PCT Pub. Date: Aug. 11, 2016

(65) Prior Publication Data
US 2018/0028777 A1 Feb. 1, 2018

(30) Foreign Application Priority Data

Feb. 7, 2015 (DK) .................................. 2015 00068
Jul. 29, 2015 (DK) .................................. 2015 00433

(51) Int. Cl.
*A61M 21/02* (2006.01)
*A61B 5/00* (2006.01)
(Continued)

(52) U.S. Cl.
CPC ............... *A61M 21/02* (2013.01); *A61B 5/11* (2013.01); *A61B 5/1118* (2013.01); *A61B 5/168* (2013.01);
(Continued)

(58) Field of Classification Search
CPC ......... A61B 5/11; A61B 5/1118; A61B 5/168; A61B 5/4824; A61B 5/486;
(Continued)

(56) References Cited

U.S. PATENT DOCUMENTS

2006/0052727 A1   3/2006  Palestrant
2011/0015468 A1*  1/2011  Aarts .................. A61B 5/0205
                                                        600/26
(Continued)

FOREIGN PATENT DOCUMENTS

CN    101969850 A    2/2011
CN    102131551 A    7/2011
EP      2196138 A3   6/2010

OTHER PUBLICATIONS

Chinese office action and search report for CN 201680017426.5 dated Dec. 26, 2019.

*Primary Examiner* — Christine H Matthews
(74) *Attorney, Agent, or Firm* — Polsinelli PC; Ron Galant

(57) ABSTRACT

The present disclosure provides a system and a method for relaxation and cultivation of attention. The method comprising: detecting a non-respiratory bodily action of a first person; determining based on comparing the non-respiratory bodily action of the first person with at least one predetermined threshold, whether or not the first person is voluntarily attending on the non-respiratory bodily action at the present time; and generating feedback to be perceived by the first person through at least one response system if the first person is voluntarily attending on the non-respiratory bodily action at the present time.

12 Claims, 22 Drawing Sheets

(51) Int. Cl.
*A61B 5/11* (2006.01)
*A61B 5/16* (2006.01)
*G05B 11/01* (2006.01)
*G09B 19/00* (2006.01)
*A61M 21/00* (2006.01)

(52) U.S. Cl.
CPC ............ *A61B 5/486* (2013.01); *A61B 5/4824* (2013.01); *A61B 5/4836* (2013.01); *A61B 5/4854* (2013.01); *A61B 5/6891* (2013.01); *A61B 5/6893* (2013.01); *A61B 5/6896* (2013.01); *A61B 5/6897* (2013.01); *A61B 5/6898* (2013.01); *A61B 5/742* (2013.01); *A61B 5/7405* (2013.01); *A61B 5/7455* (2013.01); *G05B 11/011* (2013.01); *G09B 19/00* (2013.01); *A61B 5/6887* (2013.01); *A61M 2021/0016* (2013.01); *A61M 2021/0022* (2013.01); *A61M 2021/0027* (2013.01); *A61M 2021/0044* (2013.01)

(58) Field of Classification Search
CPC .. A61M 2021/0022; A61M 2021/0027; A61M 21/02
See application file for complete search history.

(56) References Cited

U.S. PATENT DOCUMENTS

| | | |
|---|---|---|
| 2011/0140931 A1 | 6/2011 | Geurts et al. |
| 2012/0245491 A1 | 9/2012 | Amell et al. |
| 2013/0302768 A1 | 11/2013 | Webb |

\* cited by examiner

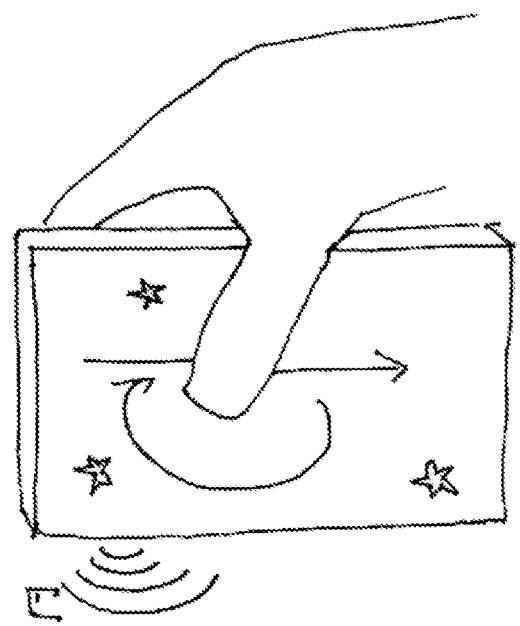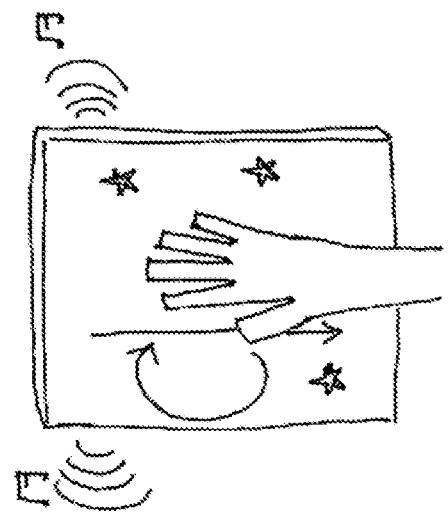
Figure 9

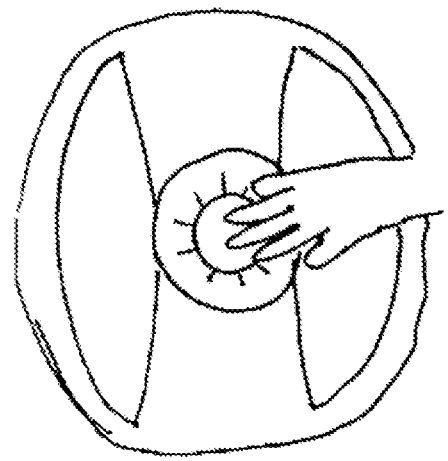
Logo on a steering wheel
Figure 13
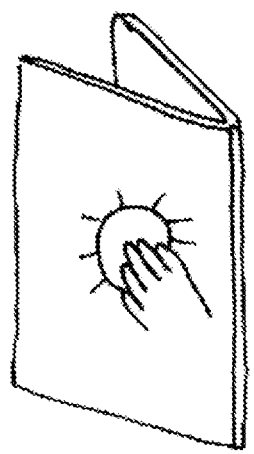
Logo on a computer

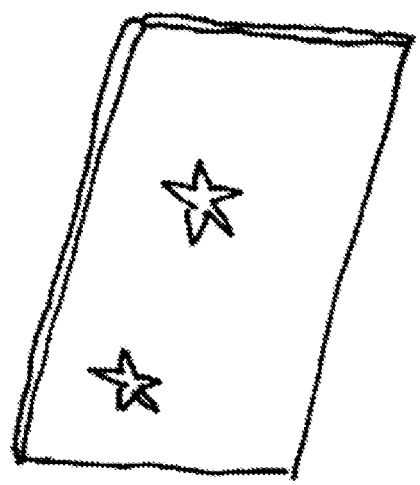
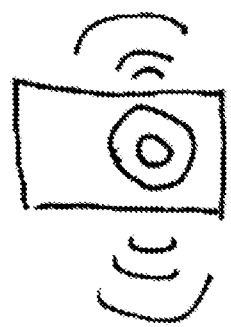
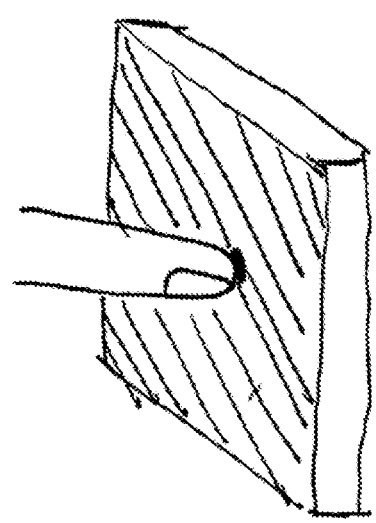
Figure 16

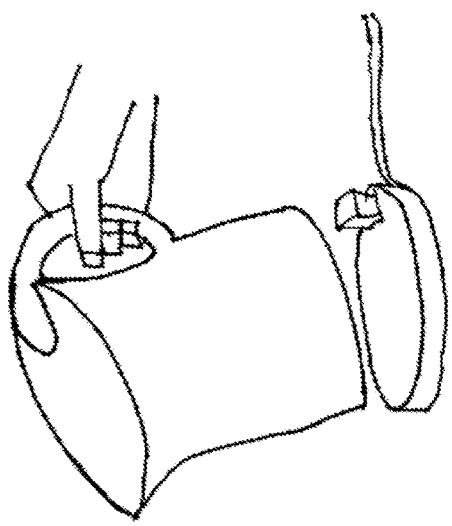
electronic water kettle
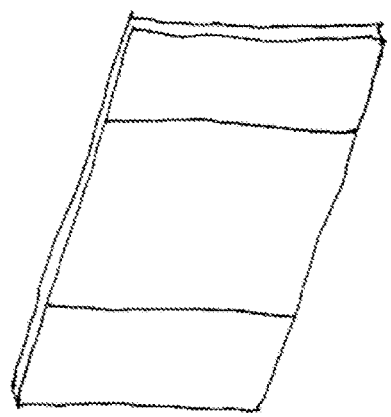
Figure 20
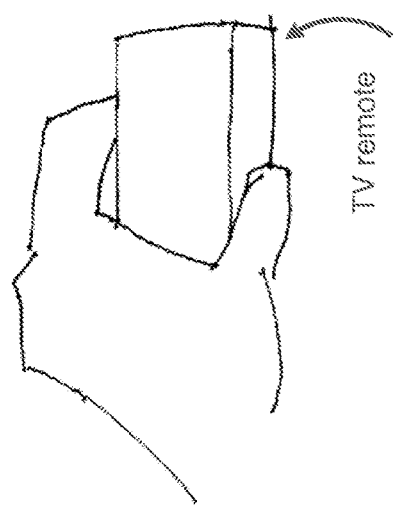
TV remote

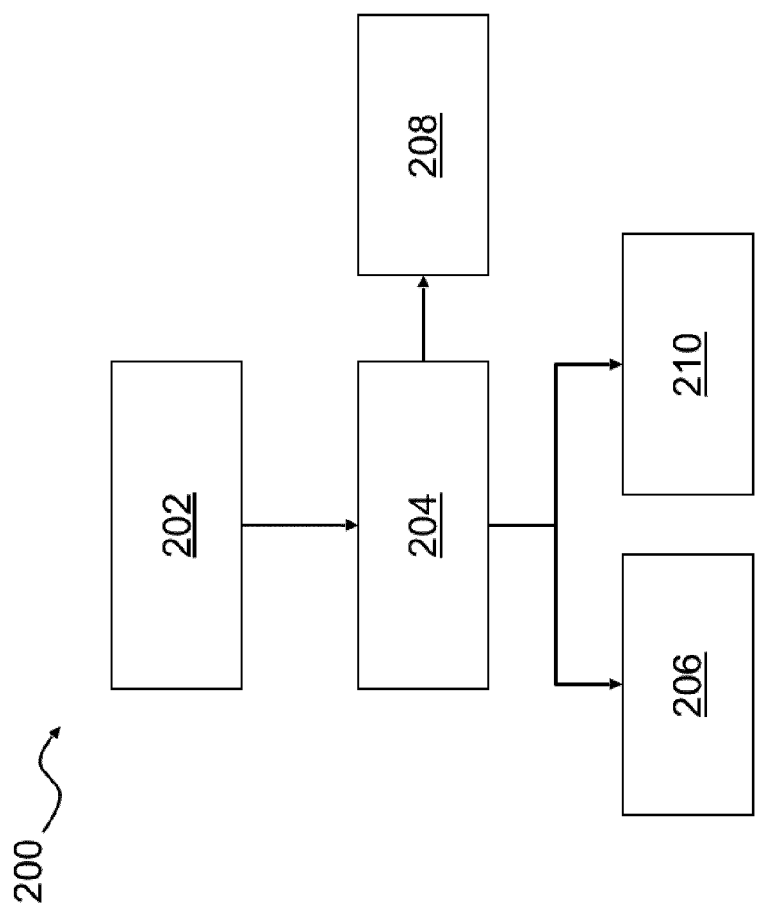

SYSTEM FOR TRACKING MOTION OF A DEVICE

SUMMARY OF THE INVENTION

The disclosure relates to systems and methods for improved motion tracking of a device, such as systems and methods for technology mediated stress relieving, well-being exercises and attention training.

BACKGROUND

Stress is a major contributing factor to the six leading causes of death in the United States: cancer, heart disease, accidents, respiratory disorders, cirrhosis of the liver and suicide. Leading medical experts estimate that 90% of disease is caused or complicated by stress. Even mild chronic stress negatively impacts one's health, physiology, and ability to learn and perform.

The word 'stress' here refers to distress, which differs from eustress, the 'positive' stress which prepares our bodies to adapt to changing demands of the environment in optimal ways. When a situation is perceived as stressful, our bodies release hormones to increase heart rate, breathing rate, blood pressure, metabolic rate and blood flow to the muscles, gearing our bodies either to do battle with an opponent or to flee, this is the so called 'fight-or-flight' stress response. While the stress response is natural and has evolved to protect the body, it is the distress, the prolonged or repeated triggering or the inability to return to a neutral state that finally causes damage as the body is preoccupied with preparing to react rather than healing itself.

In modern society, absolute stressors, such as physical threats to our safety, are rare. It is often the negative thoughts in our heads prolong and accumulate stress in our mind and body, while the stressors are actually not present in the here and now. This phenomenon is deeply rooted in one of our important cognitive capabilities: mind-wandering. Mind-wandering is the ability to think about what is not going on here and now. Research shown that people spend 46.9 percent of their waking hours thinking about something other than what they are doing, and concluded a wandering mind is unhappy. Another study has reported that 80 percent of everyone's thoughts contain some sort of negative content. Mind-wandering is closely related to another important cognitive capability: automatic processing. Highly practiced activities become automatic and thereby require less attention to perform. This explains our 'autopilot' experience as we go through daily routines, we are able to do mundane tasks almost automatically, while intensely thinking about other things. The capability of automatic processing allows a large portion of our attention left unfocused, which enables our mind to wander away to often negative and stressful thoughts.

One key aspect of stress management is to effectively relief accumulated stress, when stressors are not present. This aspect mainly concerns with directing people's attention away from the constant stream of, often stressful and negative, thoughts. Psychologists distinguish two different kinds of attention: voluntary attention and involuntary attention. Voluntary attention is an internal process that people voluntarily directing attention. Involuntary attention is an external process that stimulus events can involuntarily capture attention.

Most existing stress relieving products take advantage of people's involuntary attention, by using technology to create external stimulus in order to involuntarily capture people's attention away from stressful thoughts. One example is sensory birthing rooms, which implemented in Nordsjaellands Hospital in Denmark. The birthing rooms are equipped with a large display panel that shows calming visual stimulus, and adaptable lighting and sound systems to capture the mother's attention through various relaxing stimulus to reduce the stress of giving birth. Paro (http://www.parorobots.com) is an interactive therapeutic robot in the form of a baby seal. It behaves as if it is alive, create stimulus such as imitating the voice of a real baby seal, cute facial and bodily expressions to capture and hold patients attention. Several products focus on technology guided breathing: Resperate (http://www.resperate.com) is a Walkman-like device that uses stimulus such as auditory tones to guide relaxed breathing to reduce stress and blood pressure. StressEraser (http://www.stress.org/certified-product-stress-eraser/) and emWave (http://www.heartmath.com/emwave-technology/) are handheld devices uses visual stimulus as guidance to slow down breathing and reduce stress. These products aim to induce a state of relaxation, where technology creates external stimulus to dominate the stress relieving process, and people passively follow.

Regarding the approach of technology capturing people's involuntary attention, U.S. 2011/0015468 describes a method of maintaining a state in a subject, by measuring physiological parameters of the subject, comparing the measured parameter to a lower threshold and a upper threshold, generating an output if the parameter is below the lower threshold which indicates the subject is too relaxed, or above the upper threshold which indicates the subject is too stressed. The output involuntarily captures subject's attention, in this way warns the person about own state.

The main disadvantage of this approach is that it makes people dependent on technology and external stimulus, rather than recognising everyone of us already have self-regulative skills to relief stress and support development of such skills.

Harvard professor Herbert Benson introduced the discovery of the relaxation response in 1975. The relaxation response, counteracts the stress response, is a coordinated physiological response characterised by decreased arousal, diminished heart rate, respiratory rate and blood pressure, in association with a state of "well-being". This response helps mitigate the negative effects of stress on the body and mind in an effort to return the body to homeostasis. An essential aspect is that the relaxation response can be elicited by anyone, it is a self-regulative stress relieving process.

The eliciting of the relaxation response takes advantage of people's voluntary attention. There are only two elements required to elicit the relaxation response. 1) a mental object for the person to direct and pay attention to: the repetition of a word, sound, phrase, prayer, or muscular activity. 2) passively disregarding everyday thoughts that inevitably come to mind and returning to your repetition. However, according to Professor Herbert Benson, one of the major difficulties in the elicitation of the relaxation response is "mind wandering". The key to successfully elicit the relaxation response is that a person is able to voluntarily sustain attention to an object and able to bring the attention back every time the attention wandered away. It requires practise to become aware of our wandering attention.

In terms of using muscular activity as the mental object of attention, special physical artefacts have been invented in different cultures to facilitate the anchoring of attention in order to elicitation of the relaxation response through out human history. For example, the rosary beads in the western culture, the Tibetan prayer wheel, the Chinese meditation balls (Bao Ding balls) etc. All these physical objects require users to pay attention to their muscular movements from moment to moment in order to maintain a particular movement patterns of the physical artefacts, such as smooth rotation of the two Chinese meditation balls without them touching each other. These artefacts often associate with religious meanings.

Designers and researchers have attempted to enhance these religious physical artefacts with digital augmentation. WO 2010/018485 discloses a motion detection system, such as sensor enhanced Chinese meditation balls, to detect a movement pattern of a movement occasioned by a user, and to compare the detected movement pattern with a predetermined movement pattern, and to determine coherence between the detected and the predetermined movement pattern. Feedback is provided to the user on the basis of the determined coherence parameter. Thus, the system provides feedback on how well the user is matching a predefined movement pattern.

One disadvantage of this approach is sensing the physical artefacts's movement pattern is often complex, as disclosed in WO 2010/018485, it requires determining coherence between the detected and the predetermined movement pattern, which involves rather complex detection and processing algorithms. Another disadvantage is that it depends on specially designed physical artefacts and needs to introduce new physical artefacts, often associated with strong religious roots, into people's everyday environment, even though the person has no association with that particular religion.

There does not exist a simple technological system helps people to self-regulate own psychophysiological state through non-respiratory bodily actions to effectively elicit the relaxation response, which at the same time can be seamlessly integrated products and objects already exists in people's everyday environment, without the need to introduce any new physical artefacts, to enable mass adaptation of the system.

SUMMARY

Focusing on the aspect of muscular activity, which is proposed by Professor Herbert Benson as one kind of mental object the person may voluntarily pay attention to in order to effectively eliciting the relaxation response, the present disclosure unveils a discovery of a simple and practical method to measure human voluntary attention, which is by: measuring a particular style of movement of non-respiratory bodily actions that characterised by the qualities of slow, continuous, and/or gentle, and/or repetitive. Because in order to move any part of the body in such particular way, it requires the person to voluntarily pay attention to the muscle movement of non-respiratory bodily action itself from moment to moment.

This particular style of bodily movement is found most prominently in the Chinese meditative martial art Tai Chi. One key element of the Tai Chi practise is to voluntarily sustain attention on maintaining the body moves in a slow, continuous, gentle and repetitive way, with the effect of calm the mind and body. Importantly, this particular style of moving the body can be applied to every non-respiratory bodily actions we do in our everyday lives, and in fact we are already doing it. One example is that when we caress a sleeping baby, our hands move slowly, continuously, gently and repetitively, and this kind of non-respiratory bodily actions often associate with a feeling of love, calm and kindness.

Some bodily actions are caused by respiratory actions, such as the expansion and contraction of the chest and abdomen. The term non-respiratory bodily action refers to any bodily actions are not caused by respiration.

Because the measuring of slow, continuous, and/or gentle, and/or repetitive non-respiratory bodily action is practical with simple parameters, this disclosure unveils a simple method bridges the intangible faculty of human voluntary attention with modern technology, thus enabling technology mediation.

The present disclosure unveils a discovery that it is possible to measure whether a person is voluntarily paying attention at this moment or not, by measuring a particular style of movement of non-respiratory bodily actions, characterised by the qualities of slow, continuous, and/or gentle, and/or repetitive. Because in order to move any part of the body in this particular way, it requires the person to voluntarily pay attention to the muscle movement of the non-respiratory bodily action itself to maintain it from moment to moment. This bridges the intangible faculty of human voluntary attention with technology. The disclosure describes an interactive system senses human non-respiratory bodily actions, constantly comparing sensed input signal with at least one predetermined threshold to determine whether the person is voluntarily attending to the non-respiratory bodily action he is performing, or not. If determined the person is voluntarily attending to the non-respiratory bodily action, system generates feedback to motivate the person to continuously sustain voluntary attention to the non-respiratory bodily action. Thus a feedback loop is formed to continuously motivate the person to voluntarily pay attention to the non-respiratory bodily action. This helps the person voluntarily direct and sustain attention away from stressful thoughts, and develops own skills of relieving stress and cultivating attention. Importantly, the disclosed system can be seamlessly integrated into many everyday products, to turn them into stress relieving devices, without interfering their normal functionalities. Furthermore, the system can also make voluntarily paying attention to non-respiratory bodily actions as meaningful social activities The present disclosure provides a method, such as a method for relaxation and/or cultivation of attention, and/or a method for eliciting a relaxation response and cultivating attention, and/or a method for providing a feedback for relaxation and/or cultivation of attention.

The method comprises: detecting a non-respiratory bodily action of a first person, e.g. by detection means, such as a detection unit, such as a sensor; determining, e.g. by processing means, such as signal-processing means, such as a processing unit, based on comparing the non-respiratory bodily action of the first person with at least one predetermined threshold, whether or not the first person is voluntarily attending on the non-respiratory bodily action at the present time; and generating feedback to be perceived by the first person through at least one response system if the first person is voluntarily attending on the non-respiratory bodily action at the present time.

Determining that the first person is voluntarily attending on the non-respiratory bodily action may require that the non-respiratory bodily action has a velocity and/or an angular velocity below a predetermined velocity threshold. Alternatively or additionally, the determining that the first person is voluntarily attending on the non-respiratory bodily action may require that the non-respiratory bodily action has an acceleration and/or an angular acceleration below a predetermined acceleration threshold. Alternatively or additionally, the determining that the first person is voluntarily attending on the non-respiratory bodily action may require that the non-respiratory bodily action provides a pressure less than a predetermined pressure threshold. Alternatively or additionally, the determining that the first person is voluntarily attending on the non-respiratory bodily action may require that the non-respiratory bodily action has a repetitiveness parameter below a predetermined non-repetitiveness threshold.

Also disclosed, in accordance with another aspect, is a method, such as a method for relaxation and/or cultivation of attention, and/or a method for eliciting a relaxation response and cultivating attention, and/or a method for providing a feedback for relaxation and/or cultivation of attention.

The method comprises: detecting, e.g. by detection means, such as a detection unit, such as a sensor, a plurality of non-respiratory bodily action of a plurality of persons including a first person and a second person; determining, e.g. by processing means, such as signal processing means, such as a processing unit, based on comparing the plurality of non-respiratory bodily actions with at least one predetermined threshold, whether or not the plurality of persons are voluntarily attending on the non-respiratory bodily action at the present time; and generating feedback to be perceived by the plurality of persons through at least one response system if each of the plurality of persons are voluntarily attending on the non-respiratory bodily action at the present time.

Determining that the plurality of persons are voluntarily attending on the non-respiratory bodily action may require that each of the plurality of non-respiratory bodily actions have a velocity below a predetermined velocity threshold. Alternatively or additionally, determining that the plurality of persons are voluntarily attending on the non-respiratory bodily action may require that each of the plurality of non-respiratory bodily actions have an acceleration and/or an angular acceleration below a predetermined acceleration threshold. Alternatively or additionally, determining that the plurality of persons are voluntarily attending on the non-respiratory bodily action may require that each of the plurality of non-respiratory bodily actions provide a pressure less than the predetermined pressure threshold, and/or that each of the plurality of non-respiratory bodily actions have a repetitiveness parameter below the predetermined non-repetitiveness threshold.

Also disclosed, in accordance with another aspect, is a system, such as a system for relaxation and/or cultivation of attention, and/or a system for eliciting a relaxation response and cultivating attention, and/or a system for providing a feedback for relaxation and/or cultivation of attention.

The system comprises: a detection unit, such as a sensor, at least one response system, and a processing unit. The detection unit is configured for detecting a non-respiratory bodily action of a first person and generating at least one real-time non-respiratory bodily action signal input indicative of the non-respiratory bodily action. The at least one response system is configured for generating feedback to be perceived by the first person. The processing unit is connected to the detection unit and the at least one response system. The processing unit is configured to receive the at least one real-time non-respiratory bodily action signal input, and determine, based on comparing the at least one real-time non-respiratory bodily action signal input with at least one predetermined threshold, whether or not the first person is voluntarily attending on the non-respiratory bodily action at the present time. The processing unit is further configured to generate feedback through the at least one response system if the first person is voluntarily attending on the non-respiratory bodily action at the present time.

Determining that the first person is voluntarily attending on the non-respiratory bodily action may require that the non-respiratory bodily action has a velocity and/or an angular velocity below a predetermined velocity threshold. Alternatively or additionally, the determining that the first person is voluntarily attending on the non-respiratory bodily action may require that the non-respiratory bodily action has an acceleration and/or an angular acceleration below a predetermined acceleration threshold. Alternatively or additionally, the determining that the first person is voluntarily attending on the non-respiratory bodily action may require that the non-respiratory bodily action provides a pressure less than a predetermined pressure threshold. Alternatively or additionally, the determining that the first person is voluntarily attending on the non-respiratory bodily action may require that the non-respiratory bodily action has a repetitiveness parameter below a predetermined non-repetitiveness threshold.

Such methods and/or system enable technology to detect that a person is voluntarily paying attention, such as at this moment and/or present time. Furthermore, such methods motivate the person to voluntarily direct and sustain attention away from the stressful and negative thoughts. This may help the person effectively eliciting the relaxation response. The fact that it is the person who voluntarily sustain own attention to non-respiratory bodily action from moment to moment, cultivates the person's skill of voluntarily paying attention.

One advantage of the present disclosure is maintaining of human voluntary attention by creating an one-to-one mapping of digital feedback and voluntary attention such that the feedback only exists when voluntary attention is present. As opposed to prior art, e.g. WO2010/018485, wherein the purpose is training of skill for a particular task by giving feedback/instructions/guidance, especially when the person is doing it 'wrong', the present disclosure provides a method which may be initiated and controlled by the person himself. The feedback provided is caused by the person performing the non-respiratory bodily action. Thus, the person is in complete control of the start and end of the feedback. Thus, the person may be given the feeling of being in control.

Another advantage of the present disclosure is that moving any part of the body slowly, continuously, and/or gentle, and/or repetitive is an ability everybody already has. So it is a question of conscious choice of whether we do it or not. Therefore, the present disclosure obviates the need for technology guidance. Technology provides feedback to 'echo' the fact that the person has made the choice. So, the choice of voluntarily paying attention becomes an act with meaning (given by digital feedback). As opposed to prior art, e.g. WO 2010/018485, wherein improving skill of a particular task is about developing a skill the person does not yet have.

Furthermore, the present disclosure provides the advantage that detection may be provided by measuring simple parameters, and may be applied to any bodily movement. This means that it can be applied to any actions we do in our everyday life. As opposed to prior art, wherein the detection focus on a particular pattern of movement that the user is trying to improve.

The present disclosure furthermore has the advantage that it does not require any physical changes in the environment, or needing any new objects. For example, a table, a sofa, a wall, a phone, a tablet computer, a remote control, a shoe, a water kettle, etc. may be utilised in implementing the present disclosure. Hence, the disclosure provides a very simple way for a person to access relaxation. As long as the person chooses to move a part of his body slowly, continuously, and/or gently, and/or repetitively to interact with objects already in the physical environment, the environment will provide meaningful feedback to help sustaining the person's attention. Thereby the person's attention may be kept away from stressful thoughts, thus achieving the goal of relaxing the mind and body.

The measurement of voluntary attention may be done by measuring the movement of a non-respiratory bodily action. Measuring movement may enable the method and/or system to be easily integrated into everyday lives.

For example, the non-respiratory bodily action may be caressing, which may be applied to any objects with a surface suitable for caressing, such as a sofa, a pillow, a couch, a remote control, a table, a mobile device, a tablet computer and/or a touch sensitive screen of a mobile device, a tablet computer, and/or a wearable device. Technology such as touch sensitive textile, wood, plastic, paper, leather etc., enable many everyday objects such as our clothes, sofas, tables, pillows, steering wheels etc. become capable of measuring our caressing action. Thus, this method and/or system can be seamlessly integrated into many everyday objects, and turn them into objects can effectively help people eliciting the relaxation response.

The generated feedback may be reduced and/or adjusted if the first person and/or the plurality of persons are not voluntarily attending on the non-respiratory bodily action at the present time. Alternatively or additionally, the generated feedback may be stopped if the first person and/or the plurality of persons are not voluntarily attending on the non-respiratory bodily action at the present time.

For example, the method may further comprise reducing and/or adjusting the generated feedback if the first person and/or the plurality of persons are not voluntarily attending on the non-respiratory bodily action at the present time. Alternatively or additionally, the method may further comprise stopping the generation of feedback if the first person and/or the plurality of persons are not voluntarily attending to the non-respiratory bodily action at the present time.

Reducing and/or adjusting the generated feedback, and/or stopping the generation of feedback may be effected as soon as the person(s) is not voluntarily attending to the non-respiratory bodily action. In this way the method reminds that the person(s) is not voluntarily attending to the non-respiratory bodily action at this moment, e.g. by reducing and/or adjusting the feedback. In one embodiment, the volume of an auditory feedback may be reduced, or more noise may be added to the auditory feedback to remind the person(s) to voluntarily bring back the attention to the non-respiratory bodily action. In another embodiment, generating feedback may be stopped, e.g. to reflect that the first person and/or the plurality of persons may have purposely stopped voluntarily attending to the non-respiratory bodily action and may have continued with other activities.

The method may further comprise: monitoring the moment to moment said non-respiratory bodily action of the first person and/or plurality of persons, generating said real-time signal of said non-respiratory bodily action, and sending said real-time signal to said processing unit; wherein monitoring the moment to moment said non-respiratory bodily action is provided by sensors such as motion sensors, touch sensors, pressure sensors, audio sensors or visual sensors, which is dedicated to detect and measure said person's said non-respiratory bodily action.

The method may comprise detecting the non-respiratory bodily action of the first person and/or plurality of persons, generating the at least one real-time non-respiratory bodily action signal input indicative of the non-respiratory bodily action of the first person and/or plurality of persons, and transmitting the at least one real-time non-respiratory bodily action signal input to the processing unit.

The at least one real-time non-respiratory bodily action signal input may be detected by a detection unit. The detection unit may comprise one or more sensors. The one or more sensors may comprise one or more motion sensor(s), one or more touch sensor(s), one or more pressure sensor(s), one or more audio sensor(s) and/or one or more visual sensor(s). Motion sensor(s) may comprise one or more gyroscope(s), and/or one or more accelerometer(s), and/or one or more positional sensor(s). One or more of the one or more sensors may be comprised in a sofa, a pillow, a couch, a remote control, a table, a mobile device, a tablet computer and/or a touch sensitive screen of a mobile device, a tablet, and/or a wearable device. For example, a touch sensor may be a touch sensor of a mobile device, and/or it may be a touch sensitive surface of a couch or a sofa.

The method may further comprise: wherein said at least one response system includes for example audio, visual, tactile systems or other response systems.

The at least one response system may comprise one or more audio system(s), and/or one or more visual system(s), and/or one or more tactile system(s), and/or one or more fragrance system(s). The one or more audio system(s) may comprise one or more loudspeakers. The one or more visual system(s) may comprise one or more displays, such as a light output device, a TV display, a laptop display, a smartphone display, and/or a tablet computer display. The one or more tactile system(s) may comprise vibration unit, and/or a massage apparatus. The one or more fragrance system(s) may be configured for providing a specific fragrance, e.g. the fragrance system may comprise an apparatus for dosing perfume into the air.

The generated feedback may be configured to reflect that the first person and/or the plurality of persons are voluntarily attending to the non-respiratory bodily action, e.g. at the present time. Additionally or alternatively, the generated feedback may be configured to motivate the first person and/or the plurality of persons to keep voluntarily attending to said non-respiratory bodily action.

The generated feedback may comprise a visual output, such as light(s), such as coloured light(s).

The generated feedback may comprise one or more ambient visual(s), such as specific lighting of surroundings, such as coloured lighting of the surroundings, e.g. walls of a room.

The generated feedback may comprise an acoustic output, such as sound, such as nature sound(s), such as calm music.

The generated feedback may comprise game incentives, such as scores and/or points and/or awards, e.g. the person and/or the plurality of persons may receive a score, points, and/or an award e.g. dependent on the first person and/or the plurality of persons ability to voluntarily attending on the non-respiratory bodily action, e.g. the longer time the first person and/or the plurality of persons are voluntarily attending on the non-respiratory bodily action, the bigger score, the more points, and/or the greater an award.

The generated feedback may comprise one or more of ambient visual(s), light(s), nature sound(s), calm music, tactile feedback(s), and game incentive(s).

The generated feedback may comprise triggering of a product function. For example, the generated feedback may comprise activation and/or deactivation of a product, such as turning on a TV, turning off a TV, activating an electric water kettle, deactivating an electric water kettle etc.

For example, the system may be comprised by an electrical water kettle. The at least one response system may comprise an electrical switch for activating the electrical water kettle. The generated feedback may comprise triggering of the electrical switch. In another example, the system may be comprised by a remote control for an electrical application, e.g. a TV. The at least one response system may comprise a remote control transmitter for activating the electrical application. The generated feedback may comprise triggering of the remote control transmitter.

In one exemplary embodiment, a system may determine that the first person is voluntarily attending to a non-respiratory bodily action of using a product, the system automatically trigger a product function without requiring the first person to press a button or flip a switch. For example, voluntarily attending to the non-respiratory bodily action indicates a clear intention of the first person. It is thereby possible to simplify product interaction, by omitting certain physical interactions such as pressing a button. Such implementations of the present disclosure may encourage a person to become more mindful with daily behaviours, because products may become simpler to use if the person choose to voluntarily attending to the non-respiratory bodily actions of using everyday products.

The present disclosure provides several candidates of measurable parameters and corresponding predetermined thresholds which may be used to determine whether said person and/or plurality of persons are voluntarily attending to said non-respiratory bodily action at the present time, or not. Predetermined thresholds, such as one or more of the at least one predetermined threshold may be personalised thresholds. The measurable parameters mentioned may be used alone or in any combination.

One measurable parameter may be velocity, such as real-time velocity, of the non-respiratory bodily action, including linear velocity and/or angular velocity.

The at least one non-respiratory bodily action signal input may comprise a real-time velocity input indicative of a velocity, such as a linear velocity and/or an angular velocity, of the non-respiratory bodily action.

The at least one predetermined threshold may comprise a predetermined real-time velocity threshold, such as a predetermined linear velocity threshold and/or a predetermined angular velocity threshold. For example the predetermined velocity threshold may be between 0.2 and 5 centimetre per second, such as between 0.3 and 2 centimetre per second, such as 1.5 centimetre per second, or 1.2 centimetre per second. The predetermined velocity threshold may be dependent on the amplitude of the non-respiratory bodily action, e.g. the predetermined velocity threshold may be a first predetermined velocity threshold for a non-respiratory bodily action having a first amplitude, and a second predetermined velocity threshold for a non-respiratory bodily action having a second amplitude. The first predetermined velocity threshold may be smaller than the second predetermined velocity threshold if the first amplitude is smaller than the second amplitude.

If the velocity of the non-respiratory bodily action and/or the real-time velocity input is below the predetermined velocity threshold, the first person and/or plurality of persons may be considered as voluntarily attending on the non-respiratory bodily action at the present time. For example, if the real-time non-respiratory bodily action signal input represents that the non-respiratory bodily action has a velocity below the predetermined velocity threshold, the first person and/or plurality of persons may be considered as voluntarily attending on the non-respiratory bodily action at the present time.

If the velocity of the non-respiratory bodily action and/or the real-time velocity input is equal or above the predetermined velocity threshold, the first person and/or plurality of persons may be considered as not voluntarily attending on the non-respiratory bodily action at the present time. For example, if the real-time non-respiratory bodily action signal input represents that the non-respiratory bodily action has a velocity equal to or above the predetermined velocity threshold, said person is considered as not voluntarily attending on said non-respiratory bodily action at the present time.

Another measurable parameter may be continuity of said non-respiratory bodily action, e.g. a continuity parameter of the non-respiratory bodily action. Determining that the first person is voluntarily attending on the non-respiratory bodily action may require that the non-respiratory bodily action has a continuity parameter above a predetermined continuity threshold. Continuity may be a measure of if the first person and/or plurality of persons are performing a movement at all. The continuity parameter may be indicative of the velocity of the non-respiratory bodily action. For example, if the at least one real-time non-respiratory bodily action signal input indicates that the non-respiratory bodily action does not comprise movement, i.e. no continuity, the first person and/or plurality of persons may be considered as not voluntarily attending on the non-respiratory bodily action at the present time.

The continuity parameter may be a measure of velocity of the non-respiratory bodily action. The continuity threshold may be in the range between 0 and 0.05 cm/s, such as 0.01 cm/s and/or 0 cm/s.

For example, the at least one real-time non-respiratory bodily action signal input may comprise the continuity parameter and the method may comprise determining if the continuity parameter is indicative of a real-time velocity larger than 0.

The system may measure, e.g. by the real-time velocity input, whether said non-respiratory bodily action is moving slowly and/or continuously or not.

Another measurable parameter may be acceleration, such as real-time acceleration, of the non-respiratory bodily action, including linear acceleration and/or angular acceleration.

The at least one non-respiratory bodily action signal input may comprise a real-time acceleration input indicative of an acceleration, such as a linear acceleration and/or an angular acceleration, of the non-respiratory bodily action.

The at least one predetermined threshold may comprise a predetermined real-time acceleration threshold, such as a predetermined linear acceleration threshold and/or a predetermined angular acceleration threshold. For example the predetermined acceleration threshold may be between 0.2 and 5 centimetre per second per second, such as between 0.3 and 2 centimetre per second per second, such as 1.5 centimetre per second per second, or 1.2 centimetre per second per second.

Alternatively or additionally, the acceleration and/or acceleration threshold may be determined based on a variance or standard deviation of velocity of the non-respiratory bodily action. For example, an acceleration threshold may be a variance or standard deviation of velocity within a time duration of the non-respiratory bodily action, such as of a time duration in the range between 0.1 and 5 seconds, such as between 0.2 and 2 seconds, such as between 0.3 and 1 second. For example the acceleration threshold may be a variance or standard deviation of velocity, such as a standard deviation of velocity in the range between 0.05 and 0.5 centimetre per second, such as between 0.1 and 0.3 centimetre per second, such as 0.2 centimetre per second.

The predetermined acceleration threshold may be dependent on the amplitude of the non-respiratory bodily action, e.g. the predetermined acceleration threshold may be a first predetermined acceleration threshold for a non-respiratory bodily action having a first amplitude, and a second predetermined acceleration threshold for a non-respiratory bodily action having a second amplitude. The first predetermined acceleration threshold may be smaller than the second predetermined acceleration threshold if the first amplitude is smaller than the second amplitude.

If the acceleration of the non-respiratory bodily action and/or the real-time acceleration input is below the predetermined acceleration threshold, the first person and/or plurality of persons may be considered as voluntarily attending on the non-respiratory bodily action at the present time. For example, if the real-time non-respiratory bodily action signal input represents that the non-respiratory bodily action has an acceleration below the predetermined acceleration threshold, the first person and/or plurality of persons may be considered as voluntarily attending on the non-respiratory bodily action at the present time.

If the acceleration of the non-respiratory bodily action and/or the real-time acceleration input is equal or above the predetermined acceleration threshold, the first person and/or plurality of persons may be considered as not voluntarily attending on the non-respiratory bodily action at the present time. For example, if the real-time non-respiratory bodily action signal input represents that the non-respiratory bodily action has an acceleration equal to or above the predetermined acceleration threshold, said person is considered as not voluntarily attending on said non-respiratory bodily action at the present time.

Another measurable parameter may be time duration used for said non-respiratory bodily action to complete, or travel a certain distance or angle.

The at least one real-time non-respiratory bodily action signal input may comprise a time duration input indicative of a time duration used for the non-respiratory bodily action to complete, or travel a certain distance or angle.

The at least one predetermined threshold may comprise a predetermined time duration threshold. For example, the predetermined time duration threshold may be in the range between 0.5 and 5 seconds, such as 4 seconds, 3 seconds, 2 seconds, or 1 second. The predetermined time duration threshold may be dependent on the amplitude of the non-respiratory bodily action, e.g. the predetermined time duration threshold may be a first predetermined time duration threshold for a non-respiratory bodily action having a first amplitude, and a second predetermined time duration threshold for a non-respiratory bodily action having a second amplitude. The first predetermined time duration threshold may be smaller than the second predetermined time duration threshold if the first amplitude is smaller than the second amplitude.

If the time duration input is above the predetermined time duration threshold the first person and/or plurality of persons may be considered as voluntarily attending on the non-respiratory bodily action at the present time. For example, if the real-time non-respiratory bodily action signal input of said non-respiratory bodily action represents a time duration to complete said non-respiratory bodily action, or travel said distance or angle, which is above said predetermined time duration threshold to complete said non-respiratory bodily action, or travel said distance or angle, said person may be considered as voluntarily attending on said non-respiratory bodily action at this moment.

If the time duration input is equal to or below the predetermined time duration threshold the first person and/or plurality of persons may be considered as not voluntarily attending on the non-respiratory bodily action at the present time. For example, if the real-time non-respiratory bodily action signal input of said non-respiratory bodily action represents a time duration to complete said non-respiratory bodily action, or travel said distance or angle, which is equal or below said predetermined time duration threshold to complete said non-respiratory bodily action, or travel said distance or angle, said person may be considered as not voluntarily attending on said non-respiratory bodily action at this moment.

Thus, the system may by the time duration input measure whether said non-respiratory bodily action comprises a slow movement or not.

The system may make sure, e.g. with the use of the continuity parameter and/or continuity threshold, that a longer time duration achieved by the slow movement of said non-respiratory bodily action is not because of said non-respiratory bodily action has stopped moving.

Another measurable parameter may be pressure applied by the non-respiratory bodily action.

The at least one real-time non-respiratory bodily action signal input may comprise a pressure input indicative of pressure applied on a surface by the non-respiratory bodily action.

The at least one predetermined threshold may comprise a predetermined pressure threshold. For example, the predetermined pressure threshold may be in the range between 10 and 100 Pa, such as in the range between 15 and 50 Pa, such as 50 Pa, 30 Pa, or 15 Pa.

For example, the non-respiratory bodily action may be caressing, and the measurable parameter may be chosen to be pressure applied on a caressed surface If the pressure input is below the predetermined pressure threshold, the first person and/or plurality of persons may be considered as voluntarily attending on the non-respiratory bodily action at the present time. For example, if the real-time non-respiratory bodily action signal input of said caressing action represents a pressure below said predetermined pressure threshold, said person may be considered as voluntarily attending on said caressing action at this moment.

If the pressure input is equal to or above the predetermined pressure threshold, the first person and/or plurality of persons may be considered as not voluntarily attending on the non-respiratory bodily action at the present time. For example, if the real-time non-respiratory bodily action signal input of said caressing action represents a pressure equal or above said predetermined pressure threshold, said person may be considered as not voluntarily attending on said caressing action at this moment.

If the pressure input is 0, the first person and/or plurality of persons may be considered as not voluntarily attending on the non-respiratory bodily action at the present time. For example, if the real-time non-respiratory bodily action signal input represents said caressing action does not apply any pressure on said caressed surface, said person is considered as not voluntarily attending to said caressing action at this moment.

The system may, e.g. by using the pressure input, measure whether the non-respiratory bodily action, such as a caressing action, is performed gently or not. Another example is the act of holding a finger gently touch a surface with minimum pressure applied on the surface. This act requires the person to voluntarily sustaining attention in order to defy gravity and maintaining the minimum pressure applied on the surface from moment to moment.

Another measurable parameter may be repetitiveness of the non-respiratory bodily action, e.g. a repetitiveness parameter of the non-respiratory bodily action. For example, the repetitiveness parameter may be a time duration between a first repetition ending and a second repetition starting of the non-respiratory bodily action.

The at least one real-time non-respiratory bodily action signal input comprises a repetitiveness input indicative of time duration between a first repetition ending and a second repetition starting of the non-respiratory bodily action.

The at least one predetermined threshold may comprise a predetermined non-repetitiveness threshold. For example, the predetermined non-repetitiveness threshold may be in the range between 0.2 and 6 seconds, such as 3 second, 2 seconds, 1 second, or 0.5 seconds If the repetitiveness input is below the predetermined non-repetitiveness threshold, the first person and/or plurality of persons may be considered as voluntarily attending on the non-respiratory bodily action at the present time. For example, if the real-time non-respiratory bodily action signal input of said non-respiratory bodily action represents a time duration between previous repetition ended and starting a new repetition, which is below said predetermined threshold of time duration between previous repetition ended and starting a new repetition, said person may be considered as voluntarily attending on said non-respiratory bodily action at this moment.

If the repetitiveness input is equal to or above the predetermined non-repetitiveness threshold, the first person and/or plurality of persons may be considered as not voluntarily attending on the non-respiratory bodily action at the present time. For example, if the real-time non-respiratory bodily action signal input of said non-respiratory bodily action represents a time duration between previous repetition ended and starting a new repetition, which is equal or above said predetermined threshold of time duration between previous repetition ended and starting a new repetition, said person may be considered as not voluntarily attending on said non-respiratory bodily action at this moment.

Such a measure may be useful to measure repetitive non-respiratory bodily actions such as caressing gestures, walking, neck rotating or any repetitive muscular movement such as tapping a finger on a surface, to detect whether the person has been distracted and forgot to start a new repetition, or perhaps the person has purposely chosen to stop voluntarily attending to said non-respiratory bodily action.

Another measurable parameter may be minimum time duration that the person and/or plurality of persons has been voluntarily attending to the non-respiratory bodily action.

The method may further comprise determining an attendance time indicative of a time duration that the first person and/or the plurality of persons has been voluntarily attending to the non-respiratory bodily action. The processing unit may further be configured for determining an attendance time indicative of a time duration that the first person and/or the plurality of persons has been voluntarily attending to the non-respiratory bodily action.

The attendance time may be compared with a predetermined attendance time threshold, e.g. the method may further comprise comparing the attendance time with a predetermined attendance time threshold. For example, the predetermine attendance time threshold may be in the range between 0.5-5 seconds, such as 1 second, 3 seconds, or 5 seconds. Generating feedback may comprise that the feedback is only generated if the first person and/or plurality of persons has been voluntarily attending on the non-respiratory bodily action for a time duration longer than the predetermined attendance time threshold. For example, generated feedback may be generated only if the first person and/or plurality of persons have been voluntarily attending on said non-respiratory bodily action longer than the predetermined time duration threshold.

Such a measure may help to avoid mis-triggering of the generated feedback. For example, the system and/or method may be provided such that it will only generate feedback after the system and/or method has determined that the person and/or plurality of persons has been voluntarily attending to said non-respiratory bodily action for more than 5 seconds.

The method may further comprise generating feedback through at least one response system, if plurality of persons voluntarily attending to said non-respiratory bodily action together at the present time.

For example, detecting a non-respiratory bodily action may comprise detecting a plurality of non-respiratory bodily actions of a plurality of persons including the first person and a second person. Determining may comprise determining, based on comparing the plurality of non-respiratory bodily actions with the at least one predetermined threshold, whether or not the plurality of persons are voluntarily attending on the non-respiratory bodily action at the present time. Generating feedback may comprise generating feedback to be perceived by the plurality of persons through the at least one response system if each of the plurality of persons are voluntarily attending on the non-respiratory bodily action at the present time.

Determining that the plurality of persons are voluntarily attending on the non-respiratory bodily action may require that each of the plurality of non-respiratory bodily actions have a velocity below the predetermined velocity threshold. Alternatively or additionally, determining that the plurality of persons are voluntarily attending on the non-respiratory bodily action may require that each of the plurality of non-respiratory bodily actions have an acceleration and/or an angular acceleration below the predetermined acceleration threshold. Alternatively or additionally, determining that the plurality of persons are voluntarily attending on the non-respiratory bodily action may require that each of the plurality of non-respiratory bodily actions provide a pressure less than the predetermined pressure threshold. Alternatively or additionally, determining that the plurality of persons are voluntarily attending on the non-respiratory bodily action may require that each of the plurality of non-respiratory bodily actions have a repetitiveness parameter below the predetermined non-repetitiveness threshold.

The generated feedback may motivate the plurality of persons to keep voluntarily attending to the non-respiratory bodily action as a social activity.

The generated feedback may be a compound feedback. For example, the generated feedback may comprise a dynamic visual composition wherein each person of the plurality of persons represents a specific colour and/or a visual pattern, such as a specific visual pattern. Alternatively or additionally, the generated feedback may comprise a dynamic sound composition wherein each person of the plurality of persons represents a specific sound and/or music instrument. Alternatively or additionally, the generated feedback may comprise other dynamic response compositions.

The plurality of persons consciously attending to said non-respiratory bodily action together may be located physically together, or they may be distributed elsewhere. For example the plurality of persons may be located in a plurality of different rooms or buildings or geographical locations. For example the first person and the second person may be located physically together, alternatively, the first person and the second person may be located in different physical locations, e.g. in separate rooms. Everyone of the plurality of persons may immediately perceive said generated feedback. In this way, voluntarily attending to the non-respiratory bodily action may become synchronous physical behaviours bringing meaningful social values. This is rooted in social psychology that synchronous physical behaviour increase empathy and relatedness, motivate and facilitate learning via imitation, and build connectedness.

Slow, continuous and/or gentle finger movement may be used to rethink touch gestures, such as existing touch gestures on smartphones, to perform interaction tasks based on properties of the movement. For example, a tapping gesture can be done in a slow, continuous way, from approaching or barely touching the display and being mindful about applying pressure slowly, evenly and/or continuously in the process of pressing down and releasing the finger. This may turn a tapping gesture into a mindful journey, wherein people needs to focus on the interaction journey itself in order to perform, and it may be readily detected by commercialized technology already on smartphones.

A potential of such described touch interaction style is that it may suggest a clear intention of the person and/or people performing the task. One example could be that a slow, continuous and/or gentle tapping on the Music app icon will play a specific song, e.g. a favorite song, best suited for the context, e.g. immediately after the finger is released. The software gets a clear intention, and may also be provided enough time to process relevant information to find the most suitable piece. In this way, it may be possible to design digital experiences to honor and motivate people to frequently exercise the innate capacity of paying attention at will, which is at core of our happiness and well-being, with tangible and enjoyable benefits to create a positive cycle of forming a mindful habit of usage for smartphones.

For example the detecting of a non-respiratory bodily action of a first person, may comprise detecting a touch gesture on a touch sensitive surface.

Determining based on comparing the non-respiratory bodily action of the first person with at least one predetermined threshold, whether or not the first person is voluntarily attending on the non-respiratory bodily action at the present time, may comprise determining based on comparing the detected touch with at least one predetermined threshold, such as comparing a pressure of the touch with a predetermined pressure threshold.

Generating feedback to be perceived by the first person through at least one response system if the first person is voluntarily attending on the non-respiratory bodily action at the present time may comprise activating a response function, such as an alternative response function and/or a response function different from a standard response function, e.g. if the detected touch provides a pressure less than the predetermined pressure threshold.

For example, a method, such as a computer implemented method, is disclosed comprising: detecting a non-respiratory bodily action of a first person; determining based on comparing the non-respiratory bodily action of the first person with at least one predetermined threshold, whether or not the first person is voluntarily attending on the non-respiratory bodily action at the present time; and activating a response function if the first person is voluntarily attending on the non-respiratory bodily action at the present time.

Determining that the first person is voluntarily attending on the non-respiratory bodily action may require that the non-respiratory bodily action has a velocity and/or an angular velocity below a predetermined velocity threshold. Alternatively or additionally, the determining that the first person is voluntarily attending on the non-respiratory bodily action may require that the non-respiratory bodily action has an acceleration and/or an angular acceleration below a predetermined acceleration threshold. Alternatively or additionally, the determining that the first person is voluntarily attending on the non-respiratory bodily action may require that the non-respiratory bodily action provides a pressure less than a predetermined pressure threshold. Alternatively or additionally, the determining that the first person is voluntarily attending on the non-respiratory bodily action may require that the non-respiratory bodily action has a repetitiveness parameter below a predetermined non-repetitiveness threshold.

The non-respiratory bodily action may comprise a touch gesture, e.g. comprising a swipe and/or a tap. The detecting of the non-respiratory bodily action of the first person may comprise detecting the touch gesture on a touch sensitive surface.

For example, a method, such as a computer implemented method, is disclosed comprising: detecting a touch gesture of a touch sensitive surface; comparing the detected touch gesture with at least one predetermined threshold, such as one or more of the predetermined thresholds described for determining that the first person is voluntarily attending on the non-respiratory bodily action; and activating a response function if the touch gesture satisfies the predetermined threshold, e.g. if the detected touch gesture provides a pressure less than a predetermined pressure threshold and/or if the detected touch gesture has a velocity and/or an angular velocity below a predetermined velocity threshold.

An advantage of one or more of the disclosed methods may be that it provides that a single object, such as an icon, may provide several functions. For example, the function may be related to the interaction with the object. Furthermore, a further advantage of one or more of the disclosed methods may be that a single object, such as an icon may configured to provide a different, such as a more useful functionality, e.g. if detected the first person is performing the interaction in a mindful way, such as if the first person is voluntarily attending on the touch gesture, e.g. if the touch gesture is slow, continuous, and/or gentle.

The method may comprise activating a standard response function, such as a normal function, if the first person is not voluntarily attending on the non-respiratory bodily action at the present time. For example, normal tapping on an icon may activate the standard response function, such as launching a program associated with the icon.

The response function may be different from the standard response function. The response function may be an alternative response function. For example the response function may comprise launching a certain part of a program, such as playing a certain music song, or showing a certain content, whereas the standard response function may comprise launching the program itself.

The response function may comprise playing a song, such as a predetermined song, such as a favorite song. The response function may comprise showing certain contents and/or data. The response function may comprise showing/playing different contents and/or data compared to the standard response function.

The response function may be related to the position of the touch on the touch sensitive surface. For example, the response function may be related to an icon shown in the position of the touch. For example, the response function may be playing of an audible output, such as a song, if the position of the touch is related to a music icon, and/or the response function may be showing a video if the position of the touch is related to a video icon.

BRIEF DESCRIPTION OF THE FIGURES

The above and other features and advantages of the present invention will become readily apparent to those skilled in the art by the following detailed description of exemplary embodiments thereof with reference to the attached drawings, in which:

FIG. 9 is an embodiment of a person voluntarily attending to caressing a touch sensitive screen of a hand held, tablet, wearable or other computational devices.

FIG. 13 shows an embodiment of product logos become capable of sensing slow, continuous caressing gesture.

FIG. 16 shows an embodiment of a person voluntarily attending to maintaining a finger gently touches a pressure sensitive surface.

FIG. 20 shows two embodiments of generated feedback as triggering a product function.

FIG. 22 shows a flow chart of an exemplary method.

DETAILED DESCRIPTION

Figure 1:
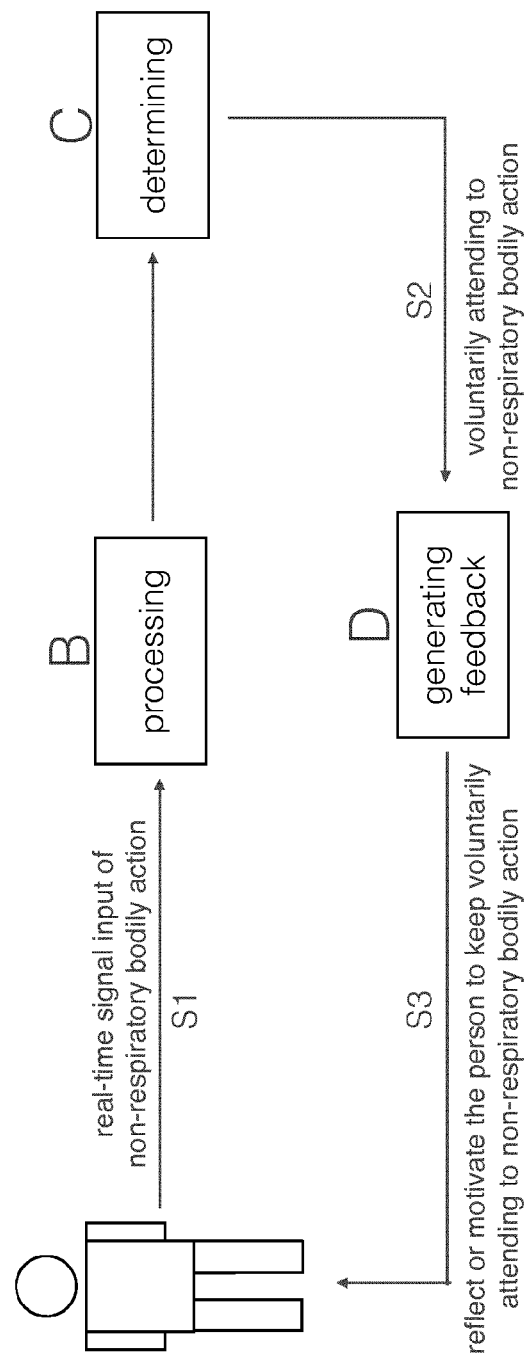
FIG. 1 is a schematic diagram of a method of motivating a person to keep voluntarily attending to a non-respiratory bodily action.

Various embodiments are described hereinafter with reference to the figures. Like reference numerals refer to like elements throughout. Like elements may, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 shows a schematic diagram of a method of motivating a person to keep voluntarily attending to a non-respiratory bodily action, comprising processing by processing unit B a real-time non-respiratory bodily action signal input S1 indicative of a non-respiratory bodily action, determining C whether said person is voluntarily attending to said non-respiratory bodily action at this moment or not, by constantly comparing said real-time non-respiratory bodily action signal input S1 of said non-respiratory bodily action with at least one predetermined threshold. If said person is voluntarily attending to said non-respiratory bodily action S2, generating feedback D to reflect that said person is voluntarily attending to said non-respiratory bodily action at this moment, or to motivate said person to keep voluntarily attending to said non-respiratory bodily action S3.

The non-respiratory bodily action may be detected by sensors such as motion sensors, touch sensors, pressure sensors, audio sensors or visual sensors, which is dedicated to detect and measure said person's said non-respiratory bodily action. The sensors may provide the real-time non-respiratory bodily action signal input S1 based on the detected non-respiratory bodily action.

Figure 2:
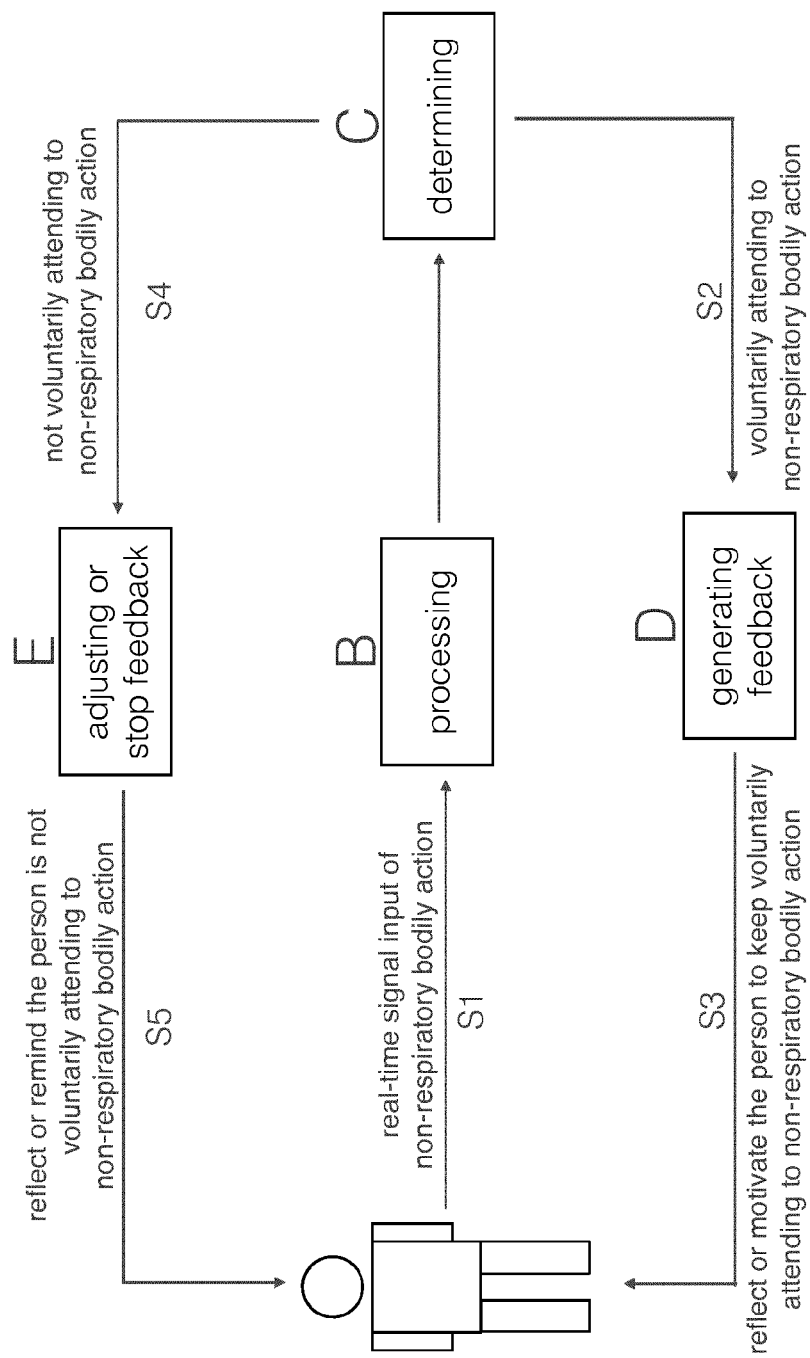
FIG. 2 is a further schematic of FIG. 1, with addition of reminding a person is not voluntarily attending to non-respiratory bodily action at this moment.

FIG. 2 shows a further schematic of FIG. 1, with addition of if said person is not voluntarily attending to said non-respiratory bodily action S4, adjusting said feedback or stop generating feedback E to remind said person is not voluntarily attending to said non-respiratory bodily action at this moment, or to reflect said person has on purposely stopped voluntarily attending to said non-respiratory bodily action S5.

Figure 3:
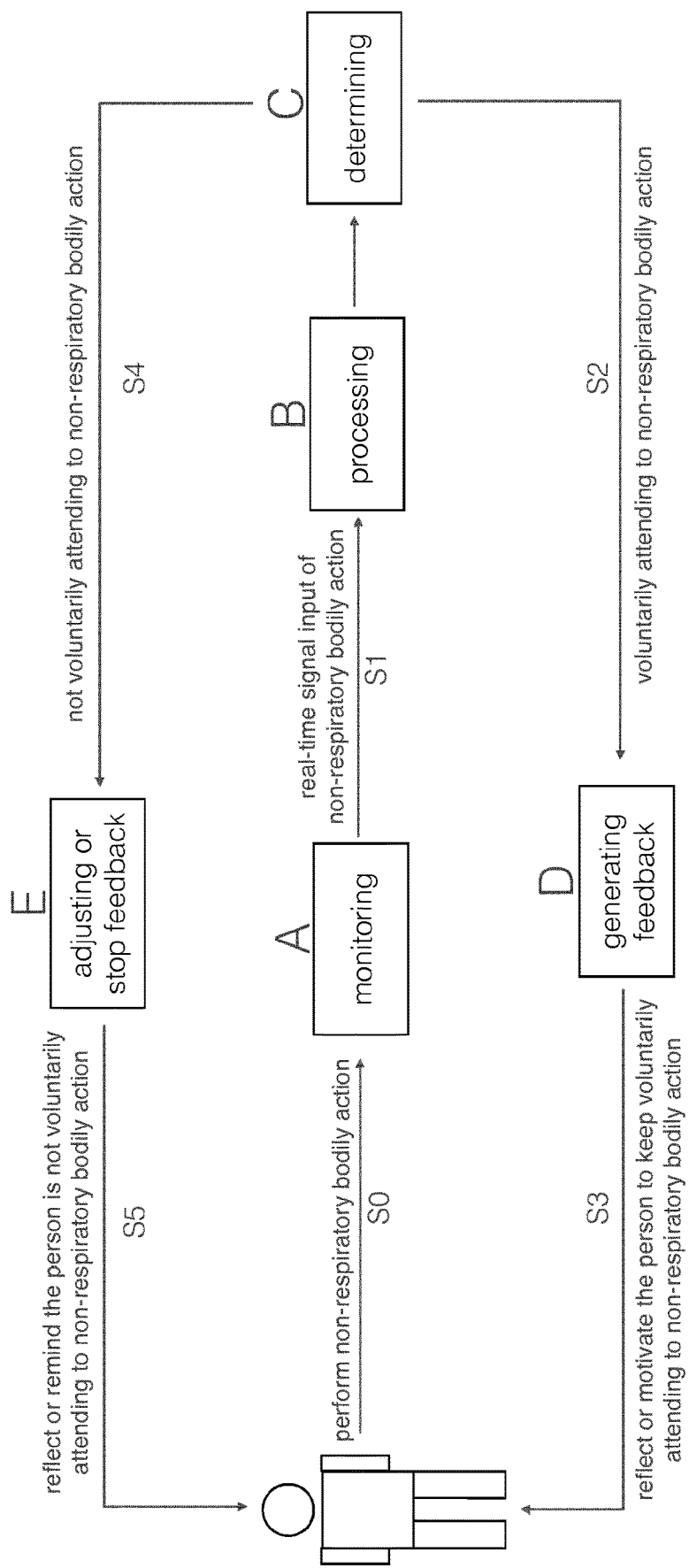
FIG. 3 is a further schematic of FIG. 2, with addition of the element of monitoring said person performing non-respiratory bodily action.

FIG. 3 shows a further schematic of FIG. 2, with addition of the element of monitoring A said person performing non-respiratory bodily action S0, by sensors such as motion sensors, touch sensors, pressure sensors, audio sensors or visual sensors, which is dedicated to detect and measure said person's said non-respiratory bodily action.

Figure 4:
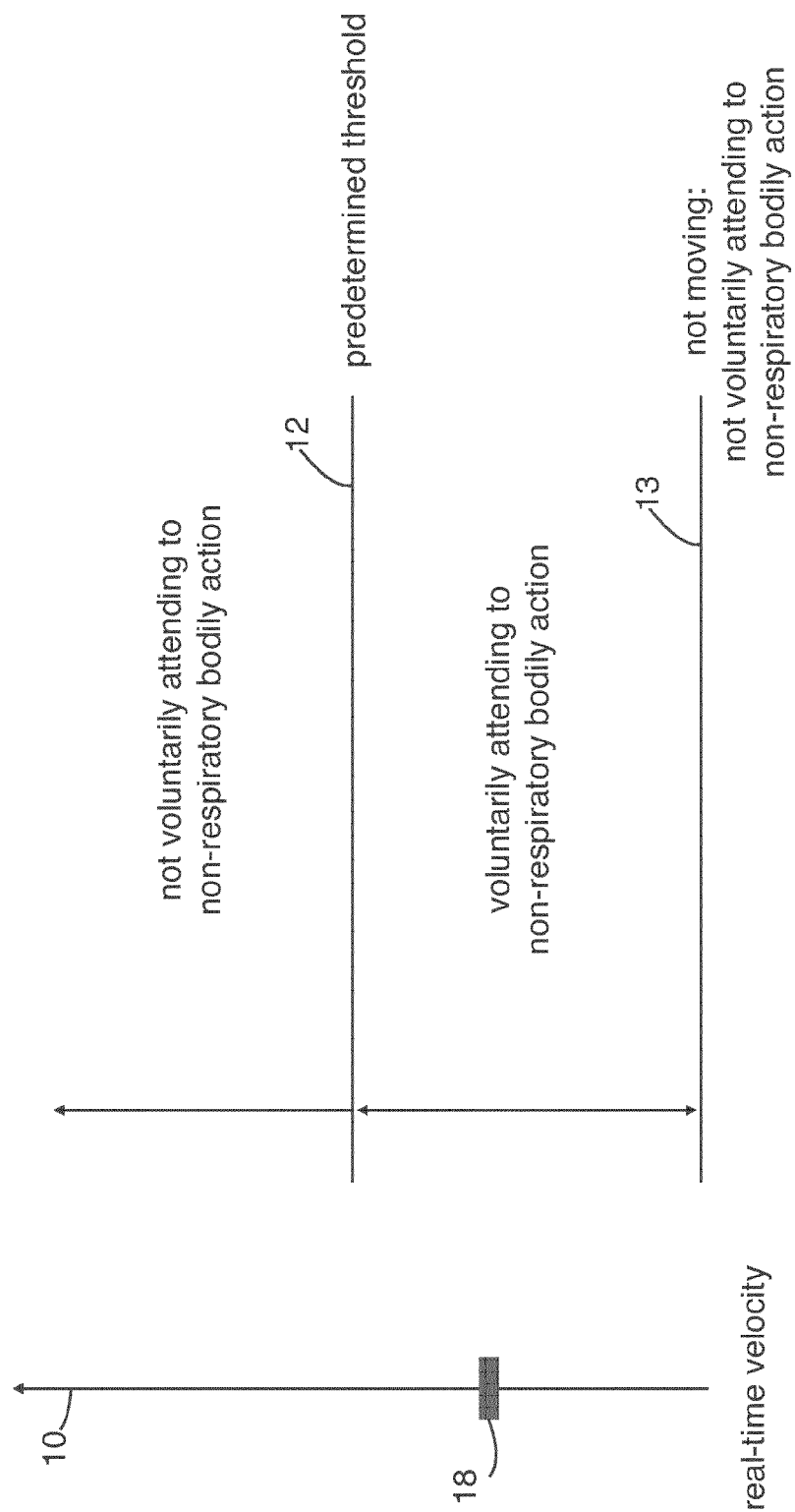
FIG. 4 is a schematic indication of using real-time velocity of said non-respiratory bodily action as measuring parameter to determine whether said person is voluntarily attending to non-respiratory bodily action at this moment or not.

FIG. 4 shows a schematic indication 10 of using real-time velocity of said non-respiratory bodily action as measuring parameter to determine whether said person is voluntarily attending to non-respiratory bodily action at this moment or not. If the real-time non-respiratory bodily action signal input of said non-respiratory bodily action represents a real-time velocity 18 equal or above predefined threshold 12, said person is determined as not voluntarily attending to said non-respiratory bodily action at this moment. If the real-time non-respiratory bodily action signal input represents said non-respiratory bodily action is moving with a real-time velocity 18 below predefined threshold 12, said person is determined as voluntarily attending to said non-respiratory bodily action at this moment. If the real-time non-respiratory bodily action signal input represents said non-respiratory bodily action not comprising movement 13, said person is determined as not voluntarily attending to said non-respiratory bodily action at this moment.

Figure 5:
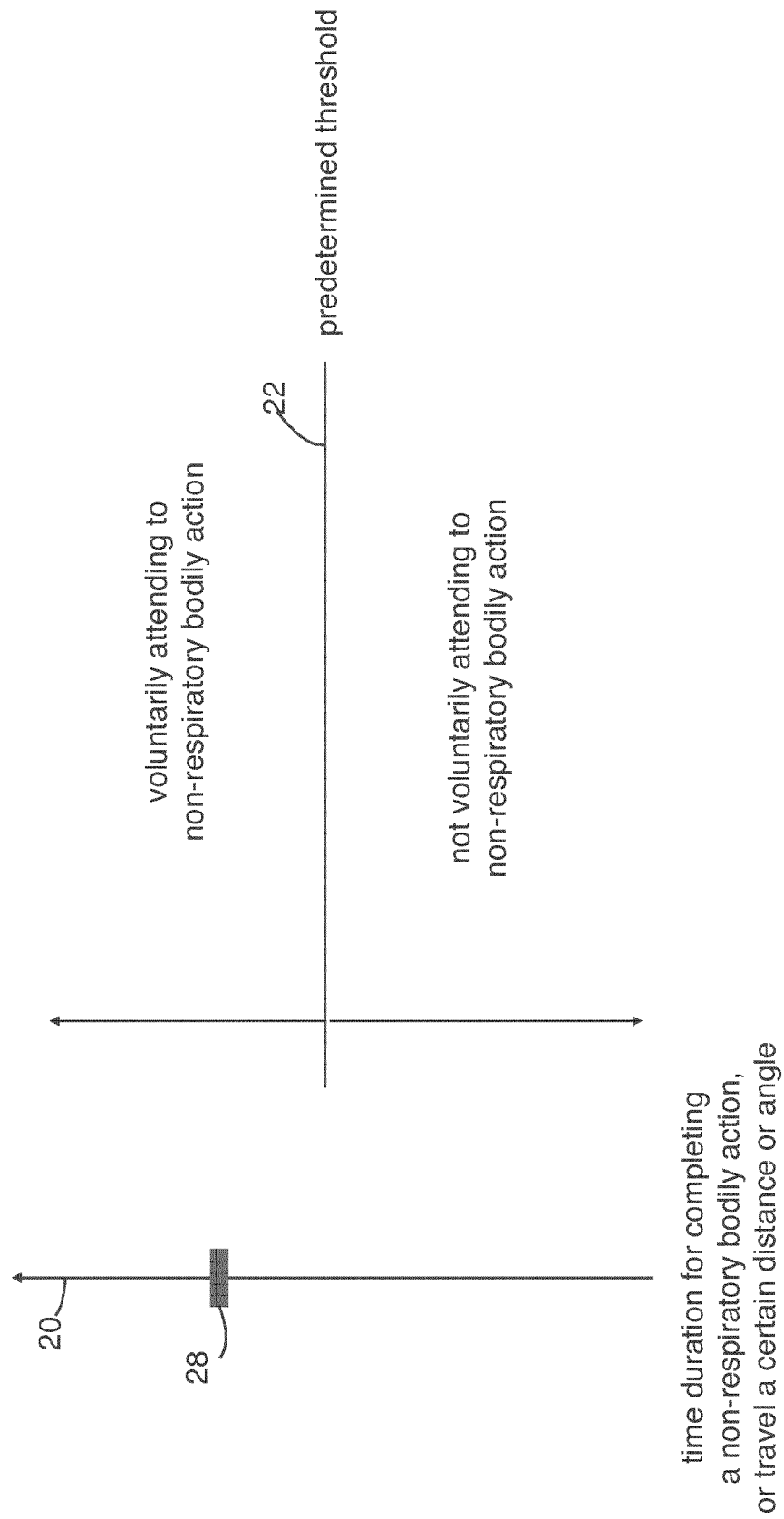
FIG. 5 is a schematic indication of using time duration used for said non-respiratory bodily action to complete, or travel a certain distance or angle as measuring parameter to determine whether said person is voluntarily attending to non-respiratory bodily action at this moment or not.

FIG. 5 shows a schematic indication 20 of using time duration used for said non-respiratory bodily action to complete, or travel a certain distance or angle as measuring parameter to determine whether said person is voluntarily attending to non-respiratory bodily action at this moment or not. If said real-time non-respiratory bodily action signal input of said non-respiratory bodily action represents a time duration to complete said non-respiratory bodily action, or travel said distance or angle 28, which is above said predetermined time duration threshold to complete said non-respiratory bodily action, or travel said distance or angle 22, said person is considered as voluntarily attending on said non-respiratory bodily action at this moment. If said real-time non-respiratory bodily action signal input of said non-respiratory bodily action represents a time duration to complete said non-respiratory bodily action, or travel said distance or angle 28, which is equal or below said predetermined time duration threshold to complete said non-respiratory bodily action, or travel said distance or angle 22, said person is considered as not voluntarily attending on said non-respiratory bodily action at this moment.

Figure 6:
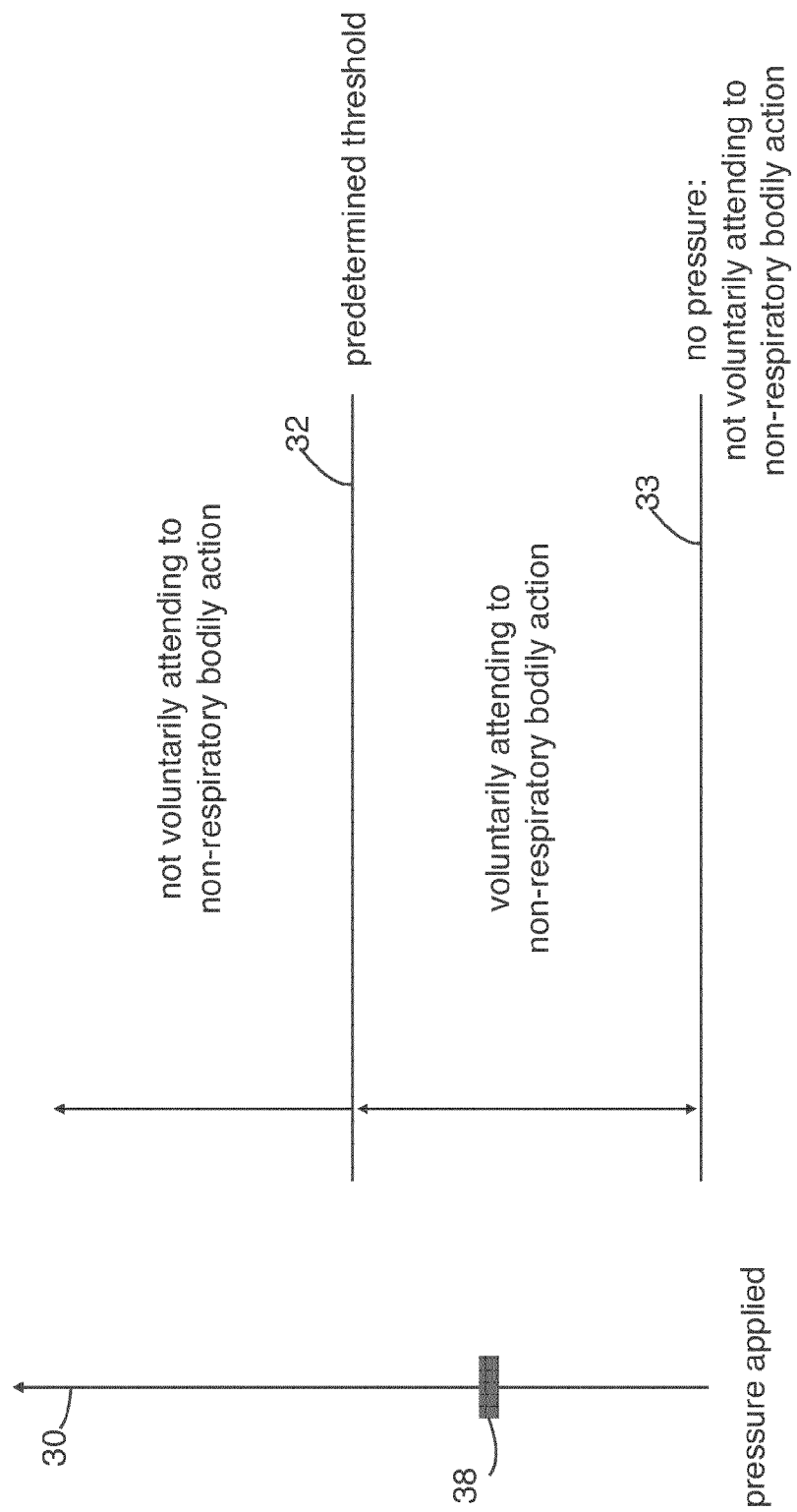
FIG. 6 is a schematic indication of using pressure applied of said non-respiratory bodily action as measuring parameter to determine whether said person is voluntarily attending to non-respiratory bodily action at this moment or not.

FIG. 6 shows a schematic indication 30 of using pressure applied of said non-respiratory bodily action as measuring parameter to determine whether said person is voluntarily attending to non-respiratory bodily action at this moment or not. If said real-time non-respiratory bodily action signal input of the non-respiratory bodily action, e.g. a caressing action, represents a pressure 38 below said predetermined pressure threshold 32, said person is considered as voluntarily attending on said caressing action at this moment. If said real-time non-respiratory bodily action signal input of the non-respiratory bodily action, e.g. said caressing action, represents a pressure 38 equal or above said predetermined pressure threshold 32, said person is considered as not voluntarily attending on said caressing action at this moment. If said real-time non-respiratory bodily action signal input represents the non-respiratory bodily action, e.g. said caressing action, does not apply any pressure 33 on said caressed surface, said person is considered as not voluntarily attending to said caressing action at this moment.

Figure 7:
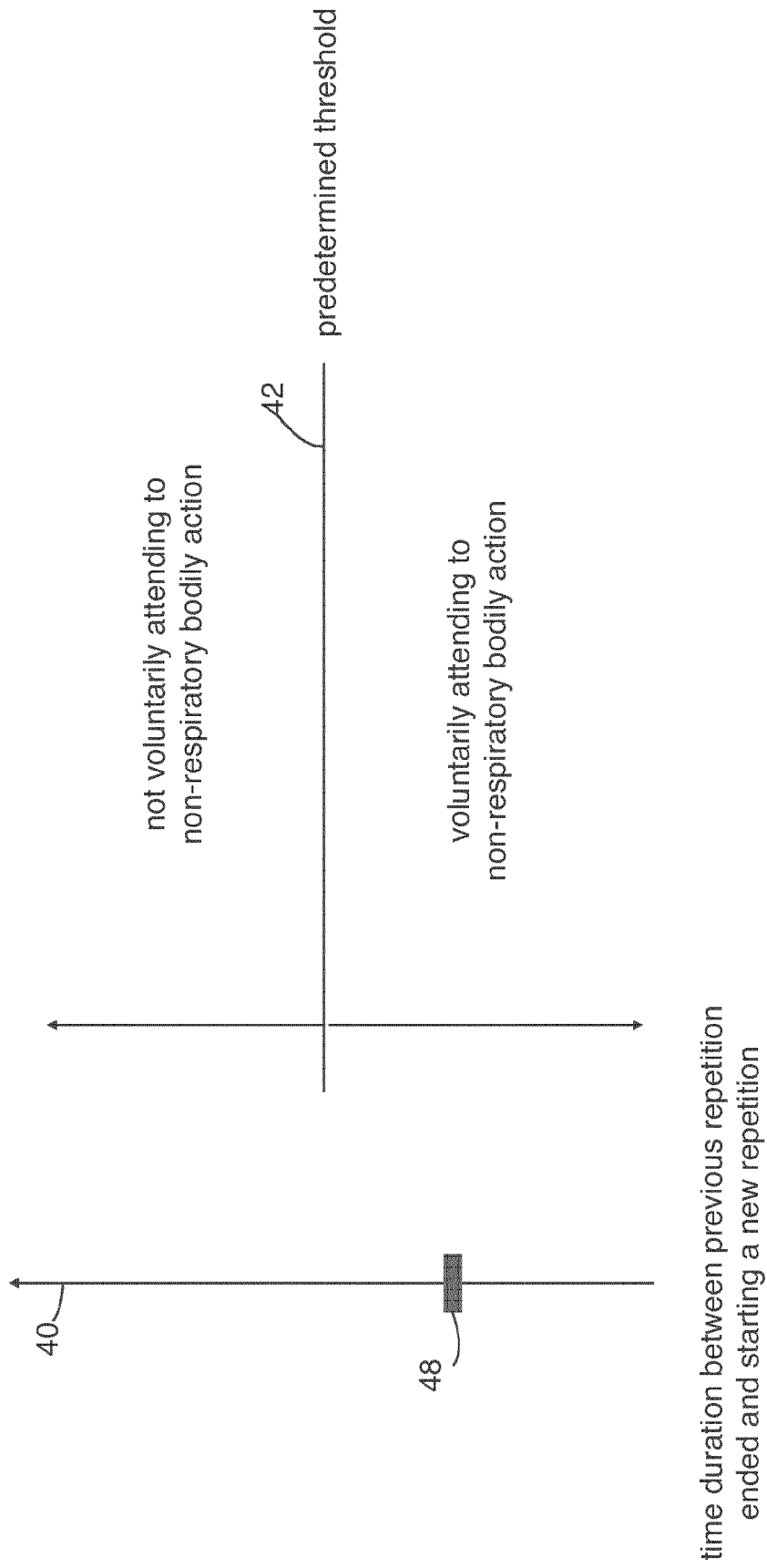
FIG. 7 is a schematic indication of using time duration between previous repetition ended and starting a new repetition of said non-respiratory bodily action as measuring parameter to determine whether said person is voluntarily attending to non-respiratory bodily action at this moment or not.

FIG. 7 shows a schematic indication 40 of using time duration between previous repetition ended and starting a new repetition of said non-respiratory bodily action as measuring parameter to determine whether said person is voluntarily attending to non-respiratory bodily action at this moment or not. If said real-time non-respiratory bodily action signal input of said non-respiratory bodily action represents a time duration between previous repetition ended and starting a new repetition 48, which is below said predetermined threshold of time duration between previous repetition ended and starting a new repetition 42, said person is considered as voluntarily attending on said non-respiratory bodily action at this moment. If said real-time non-respiratory bodily action signal input of said non-respiratory bodily action represents a time duration between previous repetition ended and starting a new repetition 48, which is equal or above said predetermined threshold of time duration between previous repetition ended and starting a new repetition 42, said person is considered as not voluntarily attending on said non-respiratory bodily action at this moment.

Figure 8:
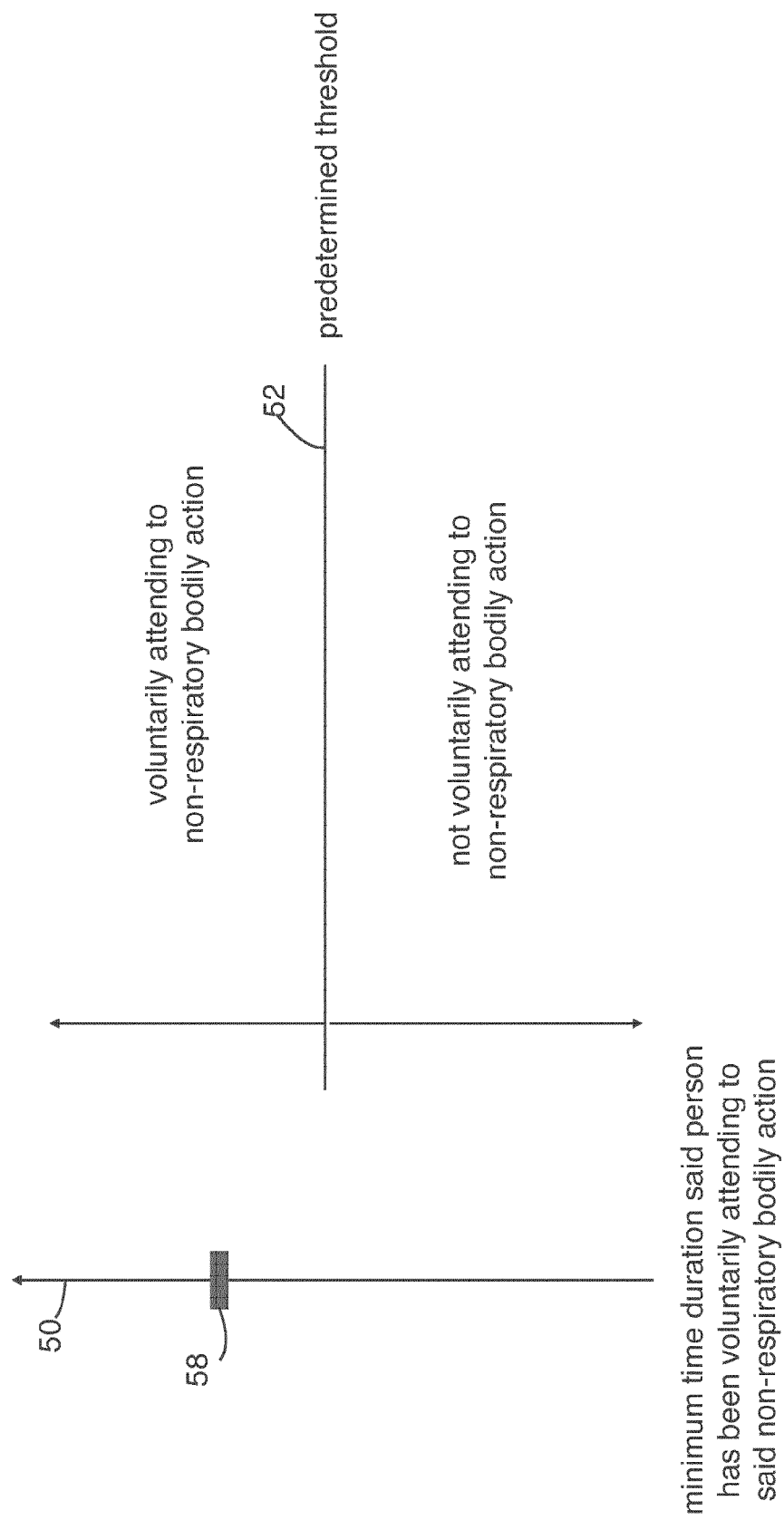
FIG. 8 is a schematic indication of using minimum time duration said person has been voluntarily attending to said non-respiratory bodily action as measuring parameter to determine whether said person is voluntarily attending to non-respiratory bodily action at this moment or not.

FIG. 8 shows a schematic indication 50 of using minimum time duration said person has been voluntarily attending to said non-respiratory bodily action as measuring parameter to determine whether said person is voluntarily attending to non-respiratory bodily action at this moment or not. If said real-time non-respiratory bodily action signal input of said non-respiratory bodily action represents a time duration of said person has been voluntarily attending to said non-respiratory bodily action 58, which is above predefined minimum time duration of said person has been voluntarily attending to said non-respiratory bodily action 52, said person is considered as voluntarily attending on said non-respiratory bodily action at this moment. Otherwise, said person is considered as not voluntarily attending on said non-respiratory bodily action at this moment.

FIG. 9 shows an embodiment of a person voluntarily attending to a non-respiratory bodily action, such as caressing a touch sensitive screen of a hand held, tablet, wearable and/or other computational devices. The device then process the real-time signal of the caressing gesture and compare with the predefined thresholds such as real-time velocity of the gesture, or time duration for completing one continuous caress repetition, to determine whether the person is voluntarily attending to the caressing gesture or not. If determined the person is voluntarily attending to the caressing gesture at this moment, the device generates feedback, for example sounds or visuals, to motivate the person to keep voluntarily attending to the slow, continuous and repetitive caressing gesture. This embodiment enables mobile devices to help people elicit the relaxation response and cultivate voluntary attention at anytime, anywhere.

Figure 10:
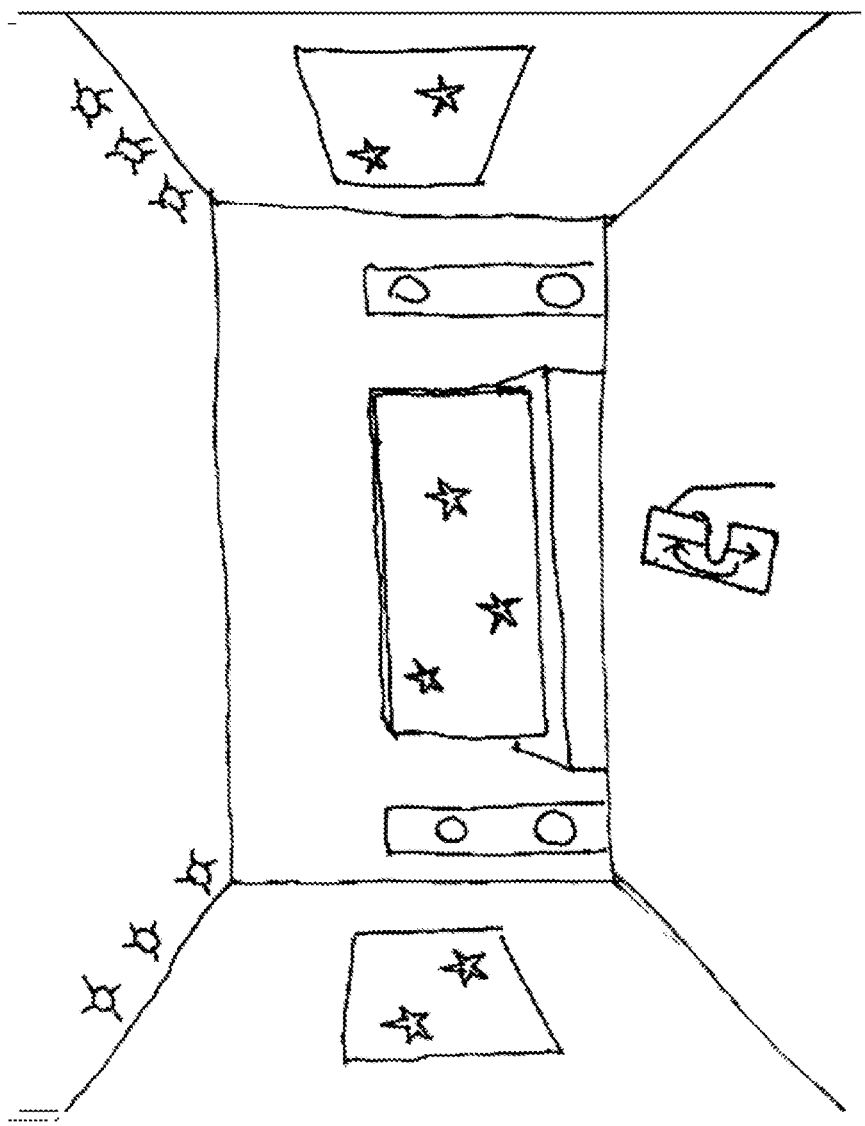
FIG. 10 is an extended embodiment of FIG. 9.

FIG. 10 shows an extended embodiment of FIG. 9. When device with touch display senses and process the real-time non-respiratory bodily action signal input of a slow, continuous and repetitive caressing gesture. If determined the person is voluntarily attending on the caressing gesture at this moment, electronic systems in the surrounding environment may generates feedback, to motivate the person to keep voluntarily attending to the slow, continuous and repetitive caressing gesture. For example, in a living room context, electronic systems that generate feedback may include TV, stereo system, and lighting system. In an in-vehicle context, electronic systems that generate feedback may include infotainment system, dashboard, projected images, lighting, sound system or tactile feedback such as massage.

The advance of technology such as touch sensitive fabric may soon be integrated into everyday products, for example touch sensitive wood interface may be used to control music. Such technologies may enable that many everyday objects can be enhanced with touch sensitive capabilities.

Figure 11:
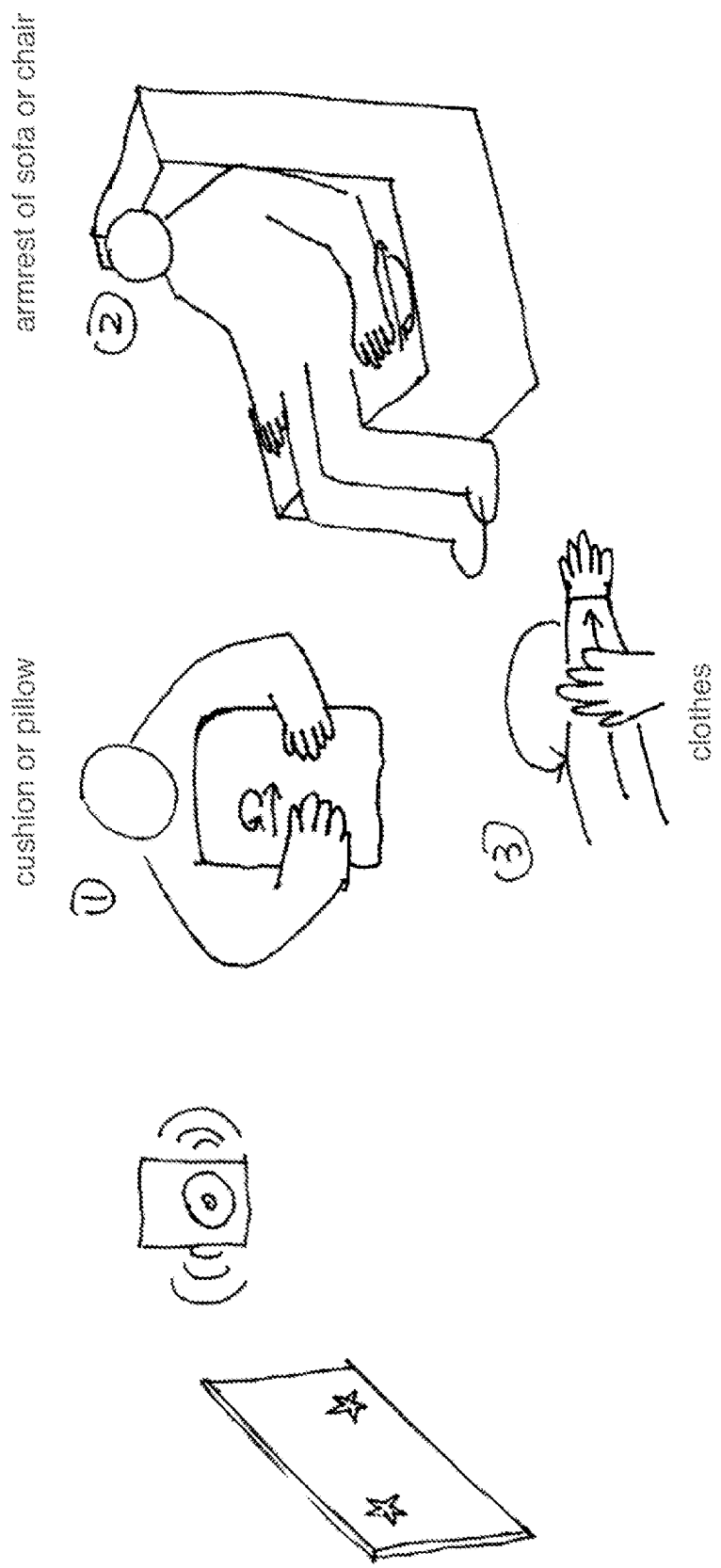
FIG. 11 shows several embodiments of everyday objects capable of sensing whether a person is voluntarily attending to a caressing gesture or not.

FIG. 11 shows several embodiments of everyday objects become capable of sensing slow, continuous and repetitive hand caressing gestures, enabled by technology such as touch sensitive fabric, wood, paper, leather, plastic etc. These objects then senses and process the real-time non-respiratory bodily action signal input of a slow, continuous and/or repetitive non-respiratory bodily action, such as a slow, continuous and/or repetitive caressing gesture. If determined the person is voluntarily attending on the caressing gesture at this moment, feedback are generated to motivate the person to keep voluntarily attending to the slow, continuous and repetitive caressing gesture. Objects such as a cushion, pillow or a sofa are ideal for eliciting the relaxation response by performing a caressing gesture, because their main function is already providing a sense of comfort, privacy and safety. Objects such as clothes enable people to elicit the relaxation response at anywhere, anytime.

Figure 12:
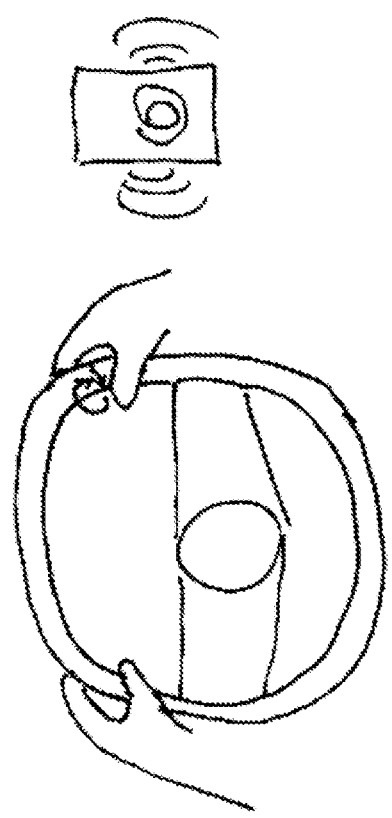
FIG. 12 shows an embodiment of the steering wheel become capable of sensing slow, continuous and repetitive caressing.

FIG. 12 shows an embodiment of the steering wheel become capable of sensing a non-respiratory bodily action, such as a slow, continuous and/or repetitive non-respiratory bodily action, such as a slow, continuous and/or repetitive caressing by the thumb, or other fingers, enabled by technology such as such as touch sensitive fabric, wood, paper, leather, plastic etc. If determined that the person is voluntarily attending to the caressing gesture at this moment, feedback are generated to motivate the person to keep voluntarily attending to keep the slow, continuous and repetitive caressing gesture. This can be used in the situation such as traffic lights or traffic jams, the driver can choose to effectively elicit the relaxation response, instead of become frustrated. Same embodiment can be applied to handlebars of bicycle or motorcycle.

FIG. 13 shows embodiments of product logos becoming capable of sensing a non-respiratory bodily action, such as a slow, continuous and/or repetitive non-respiratory bodily action, such as a slow, continuous caressing gesture. When detected the person is caressing the logo slowly and continuously, the logo lights up, e.g. to recognise that the person is treating the product with care. This is a way to enhance brand awareness and create a new relationship between the customer and the product, as if the product becomes alive when the person is treating it with care.

Figure 14:
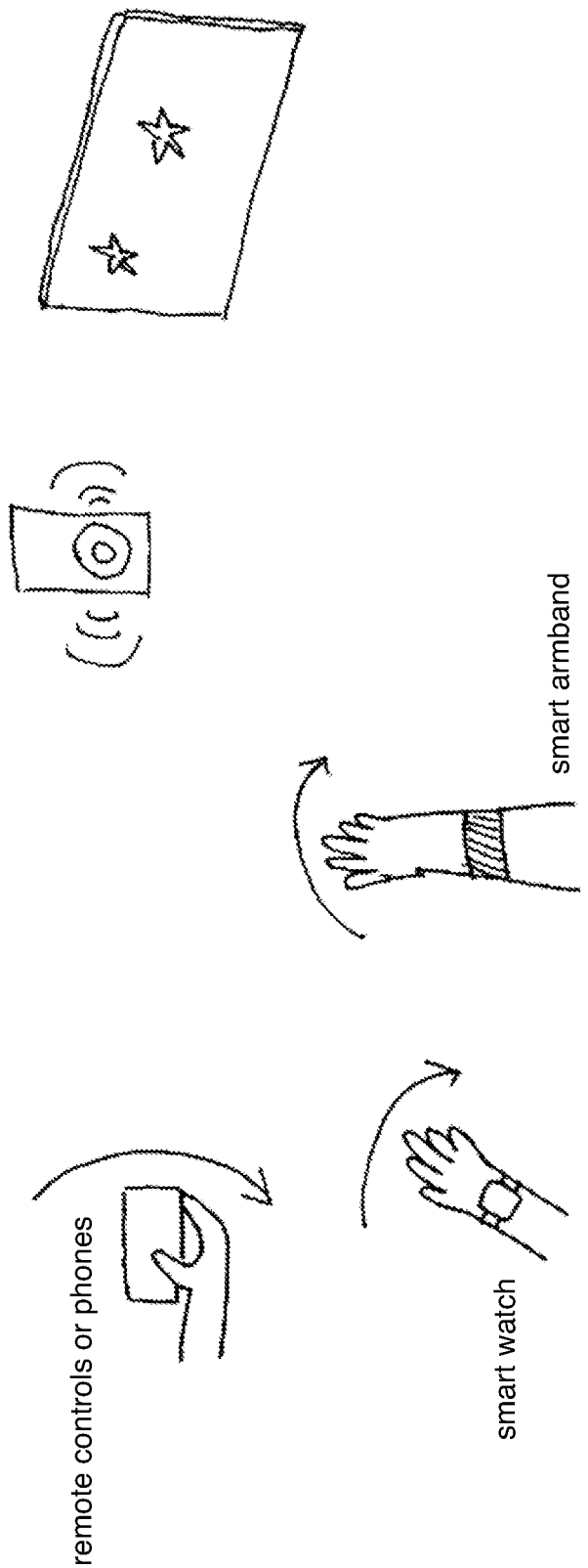
FIG. 14 shows an embodiment of digital products using built-in motion sensors to sense a slow, continuous arm movement.

FIG. 14 shows an embodiment of digital products including phones, remotes, smart watches, and smart armbands, using their built-in motion sensors to sense a non-respiratory bodily action, such as a slow and/or continuous hand or arm movement. If determined the person is voluntarily attending to the hand or arm movement at this moment, feedback are generated to motivate the person keep voluntarily attending to the slow, continuous and if necessary, repetitive hand or arm movement.

Figure 15:
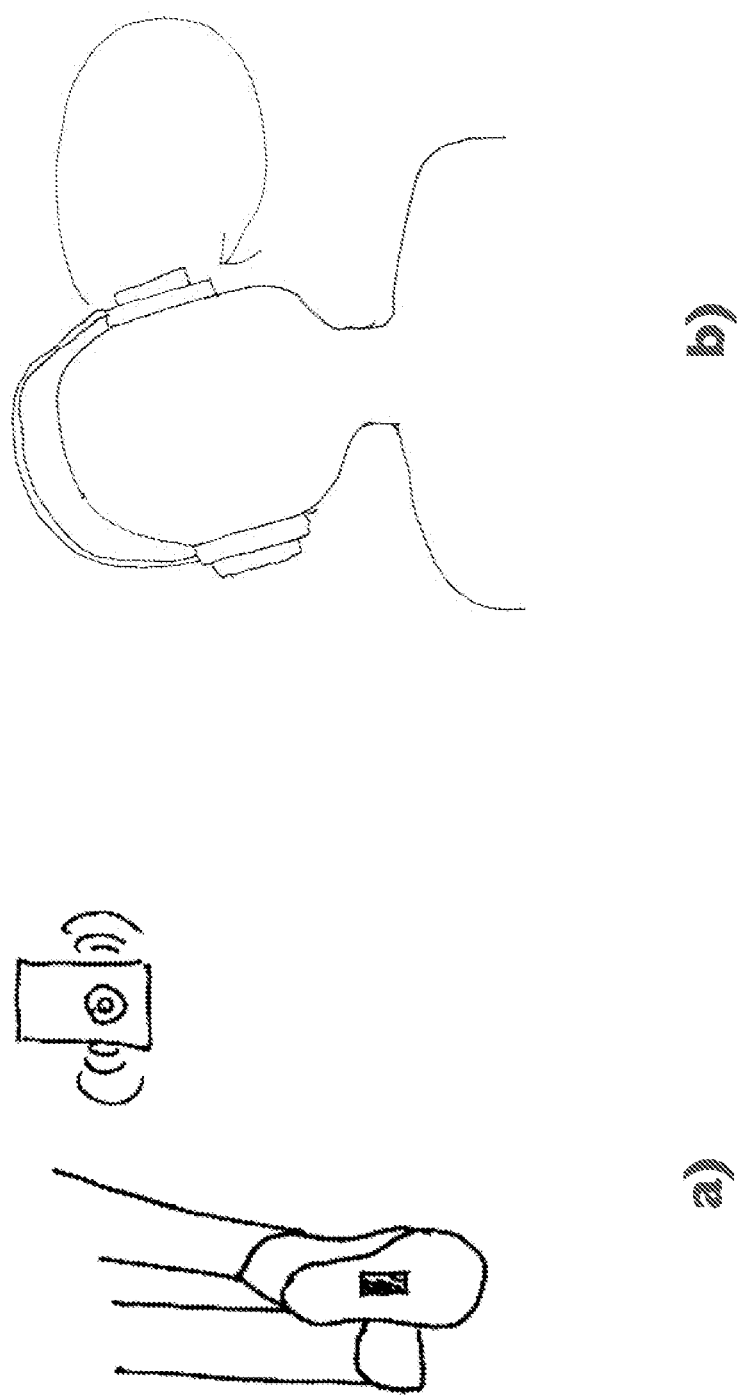
FIG. 15 shows two other embodiments of using motion sensors to sense slow, continuous non-respiratory bodily actions.

FIG. 15a shows an embodiment of shoes with built in motion sensors to sense a non-respiratory bodily action, such as a slow, continuous and/or repetitive walking movement. If determined that the person is voluntarily attending to the walking movement at this moment, feedback is generated to motivate the person keep voluntarily attending to keep the slow, continuous and/or repetitive walking movement. This is useful for people who practice mindful walking exercises.

FIG. 15b shows another embodiment of a headphone with built in motion sensors to sense a slow and/or continuous neck rotation movement. If determined that the person is voluntarily attending to the neck rotating movement at this moment, feedback is generated to motivate the person to keep voluntarily attending to keep the slow and/or continuous neck rotating movement.

FIG. 16 shows an embodiment of a person holding a finger to touch a pressure sensitive surface, and maintains the minimum pressure the finger applies to the surface. This act requires the person to voluntarily sustaining attention in order to defy gravity and maintaining the minimum pressure applied on the surface from moment to moment. Feedback is generated to motivate the person keep voluntarily attending to keep the touched pressure at minimum.

Figure 17:
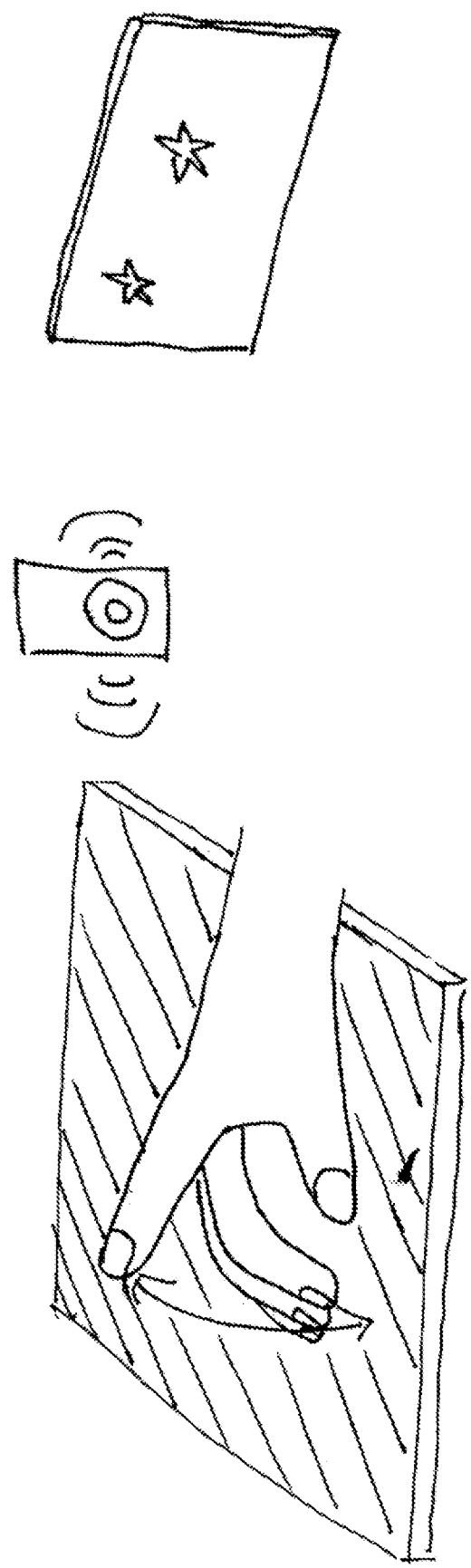
FIG. 17 shows an embodiment of a person voluntarily attending to maintaining a repetitive muscular movement such as tapping a finger on a touch sensitive surface.

FIG. 17 shows an embodiment of a person voluntarily sustaining attention on maintaining a repetitive finger tapping movement on a touch sensitive surface. Feedback is generated to motivate the person keep voluntarily attending to keep the repetitive tapping movement. This applies to any other repetitive non-respiratory bodily movements, such as tapping the feet on the floor.

Figure 18:
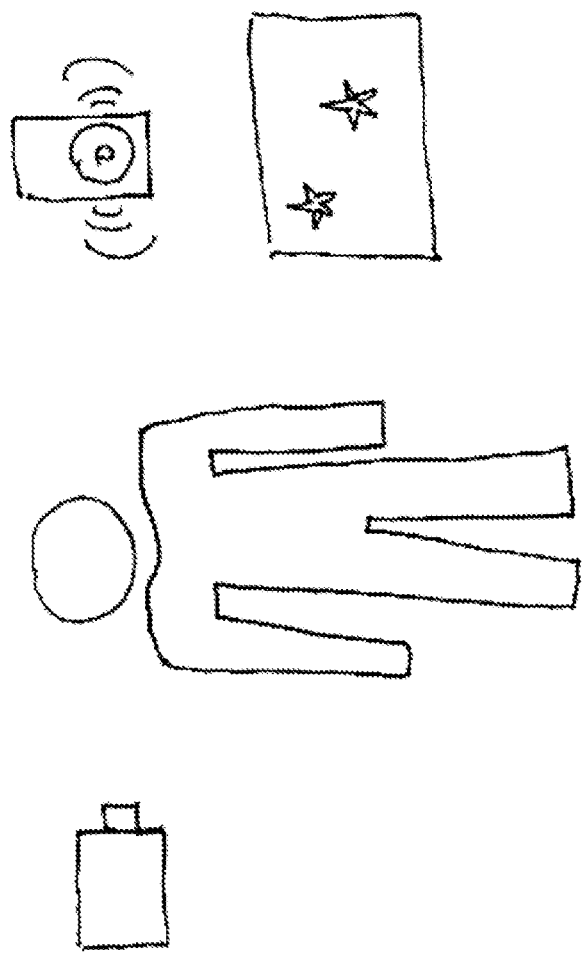
FIG. 18 shows an embodiment of using visual sensors to sense slow, continuous non-respiratory bodily actions.

FIG. 18 shows an embodiment of using visual sensors to sense a non-respiratory bodily action, such as a slow and/or continuous non-respiratory bodily action. For example, such embodiment may include products with a built in camera, such as smart phones, smart glasses, game console etc. If determined that the person is voluntarily attending to the non-respiratory bodily actions at this moment, feedback is generated to motivate the person keep voluntarily attending to the non-respiratory bodily actions.

Figure 19:
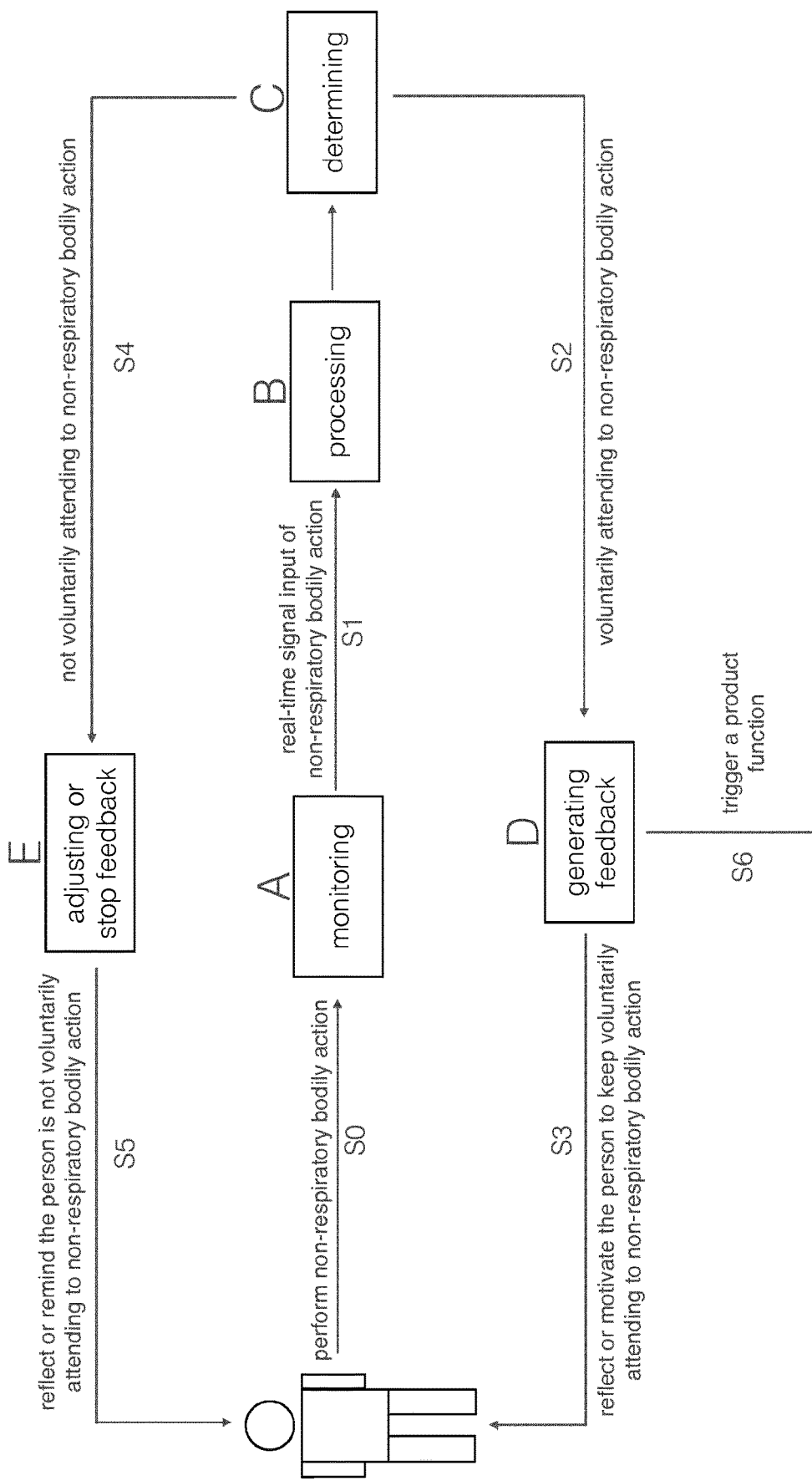
FIG. 19 is a further schematic of FIG. 3, with addition of generated feedback as triggering a product function.

FIG. 19 shows a further schematic of FIG. 3, wherein the generated feedback comprises triggering of a product function S6. Voluntarily attending to a non-respiratory bodily action of using a product, may be utilised for technology to easier understand the person's intention with said non-respiratory bodily action. For example, this may be used to simplify the interaction with said product.

FIG. 20 shows two embodiments wherein the generated feedback comprises triggering of a product function. One embodiment is by determining a person is voluntarily attending to the non-respiratory bodily action of lifting up a TV remote control, the system generates a feedback comprising automatically turning on the TV. Thereby, the TV may be turned on without requiring said person to press a physical button. Another embodiment shown is by determining that a person is voluntarily attending to the non-respiratory bodily action of putting down an electronic water kettle to its base, the system generates a feedback comprising automatically start boiling the water. Thereby the electronic water kettle may be activated without requiring said person to press a physical button.

Another embodiment (not shown) of this method may be to engage the person to maintain an already calm and peaceful environment by voluntarily attending to a non-respiratory bodily action. One example may be a person is walking by a virtual garden and seeing a butterfly stopping at a beautiful flower. If said person is determined as voluntarily attending to the walking movement, system maintains the current scene. If said person is determined as not voluntarily attending to the walking movement, system may generate a feedback, for instance the butterfly flies away, as if said person's behaviour has disturbed the peaceful scene.

Figure 21:
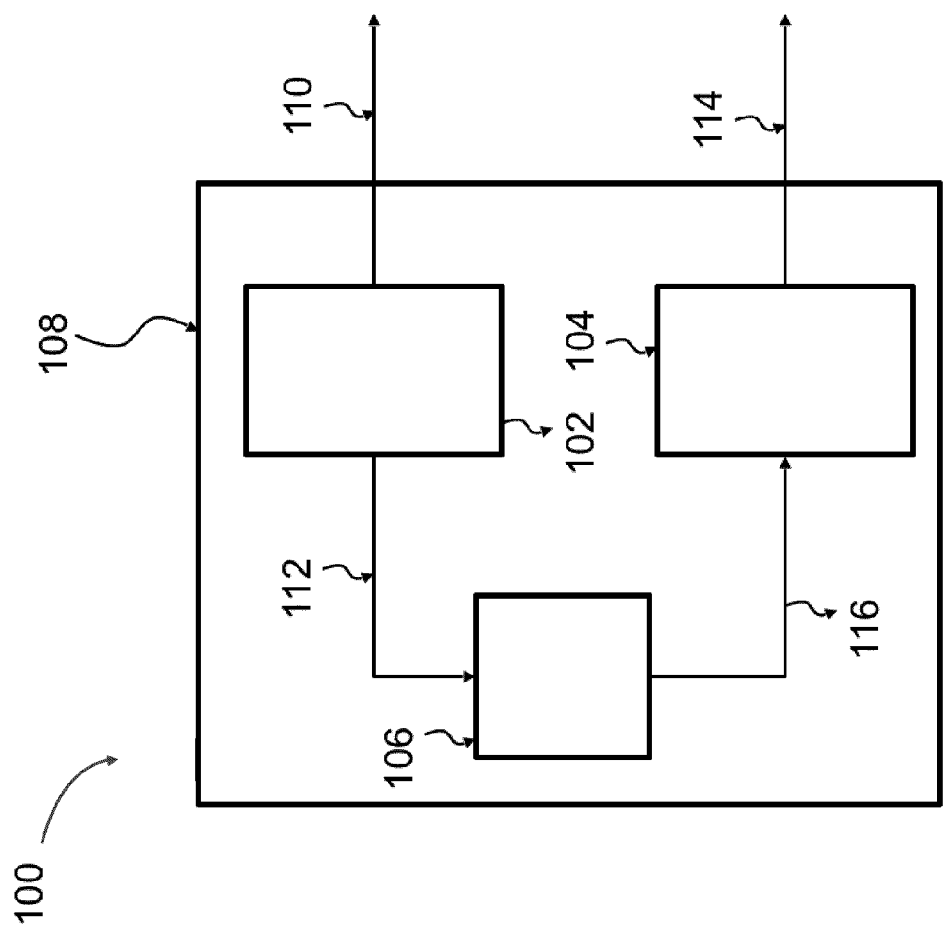
FIG. 21 schematically illustrates a block diagram of an exemplary system.

FIG. 21 schematically illustrates a block diagram of an exemplary system 100, e.g. for relaxation and cultivation of attention. The system 100 comprises a detection unit 102, a response system 104, and a processing unit 106. Furthermore the exemplary system 100 comprises an optional housing 108. The housing 108 enclose and/or comprise the detection unit 102, the response system 104, and the processing unit 106. The system 100 may comprise more than one response system 104 and/or the system 100 may comprise a plurality of detection units 102.

The detection unit 102 is configured for detecting a non-respiratory bodily action 110 of a first person (not shown). The detection unit 102 is further configured to generate one or more signal inputs, such as at least one real-time non-respiratory bodily action signal input 112, wherein the signal input and/or the at least one real-time non-respiratory bodily action signal input 112 is indicative of the non-respiratory bodily action.

The detection unit 102 may comprise one or more sensors (not shown). For example, the detection unit 102 may comprise one or more motion sensor(s), and/or one or more touch sensor(s), and/or one or more pressure sensor(s), and/or one or more audio sensor(s), and/or one or more visual sensor(s).

The response system 104 is configured for generating feedback 114. The generated feedback 114 is to be perceived by the first person. The response system 104 may comprise output units. For example, the response system 104 may comprise one or more audio system(s), and/or one or more visual system(s), and/or one or more tactile system(s), and/or one or more fragrance system(s).

The processing unit 106 is connected to the detection unit 102 and the response system 104. The processing unit 106 is configured to receive the at least one real-time non-respiratory bodily action signal input 112. The processing unit 106 is further configured to determine, based on comparing the at least one real-time non-respiratory bodily action signal input 112 with at least one predetermined threshold, whether or not the first person is voluntarily attending on the non-respiratory bodily action 110 at the present time. The processing unit 106 is further configured to generate feedback 114 through the response system 104 if the first person is voluntarily attending on the non-respiratory bodily action 110 at the present time. The processing unit 106 may provide a feedback control signal 116 to the response system 104, indicative of the feedback to be generated by the response system 104.

FIG. 22 shows a flow chart of an exemplary method 200, e.g. for relaxation and cultivation of attention. The method 200 comprises: detecting 202 a non-respiratory bodily action of a first person, determining 204 whether or not the first person is voluntarily attending on the non-respiratory bodily action at the present time, and generating 206 feedback if the first person is voluntarily attending on the non-respiratory bodily action at the present time.

Determining 204 may be based on comparing 208 the non-respiratory bodily action of the first person with at least one predetermined threshold.

For example determining 204 may be based on velocity and/or angular velocity of the non-respiratory bodily action, e.g. determining 204 that the first person is voluntarily attending on the non-respiratory bodily action may require that the non-respiratory bodily action has a velocity and/or an angular velocity below a predetermined velocity threshold, e.g. comparing 208 may comprise comparing the velocity and/or the angular velocity of the non-respiratory bodily action with the predetermined velocity threshold.

Alternatively or additionally, determining 204 may be based on acceleration and/or angular acceleration of the non-respiratory bodily action, e.g. determining 204 that the first person is voluntarily attending on the non-respiratory bodily action may require that the non-respiratory bodily action has an acceleration and/or an angular acceleration below a predetermined acceleration threshold, e.g. comparing 208 may comprise comparing the acceleration and/or the angular acceleration of the non-respiratory bodily action with the predetermined acceleration threshold.

Alternatively or additionally, determining 204 may be based on pressure provided, e.g. on a surface, by the non-respiratory bodily action, e.g. determining 204 that the first person is voluntarily attending on the non-respiratory bodily action may require that the non-respiratory bodily action provides a pressure less than a predetermined pressure threshold, e.g. comparing 208 may comprise comparing the pressure provided by the non-respiratory bodily action with the predetermined pressure threshold.

Alternatively or additionally, determining 204 may be based on repetitiveness of the non-respiratory bodily action, e.g. determining 204 that the first person is voluntarily attending on the non-respiratory bodily action may require that the non-respiratory bodily action has a repetitiveness parameter below a predetermined non-repetitiveness threshold, e.g. comparing 208 may comprise comparing the repetetiveness parameter of the non-respiratory bodily action with the non-repetiveness threshold. The repetitiveness parameter may be a time duration between a first repetition ending and a second repetition starting of the non-respiratory bodily action.

Determining 204 that the first person is voluntarily attending on the non-respiratory bodily action may require that the non-respiratory bodily action has a continuity parameter above a predetermined continuity threshold, e.g. comparing 208 may comprise comparing the continuity parameter of the non-respiratory bodily action with the continuity threshold.

The method 200 may further comprise determination of an attendance time indicative of a time duration that the first person has been voluntarily attending to the non-respiratory bodily action. Determining 204 that the first person is voluntarily attending on the non-respiratory bodily action may require that the attendance time is above a predetermined attendance time threshold, e.g. comparing 208 may comprise comparing the attendance time with the attendance time threshold. For example, the feedback may be only generated 206 if the first person has been voluntarily attending on the non-respiratory bodily action for a time duration longer than the predetermined attendance time threshold.

The method 200 may further comprise reducing and/or adjusting and/or stopping 210 the generated feedback if the first person is not voluntarily attending on the non-respiratory bodily action at the present time.

The generated 206 feedback may be configured to reflect that the first person is voluntarily attending to the non-respiratory bodily action at the present time.

Alternatively or additionally, the generated 206 feedback may be configured to motivate the first person to keep voluntarily attending to the non-respiratory bodily action.

The method 200 may be adapted to be suitable for a plurality of persons. For example detecting 202 may comprise detecting a plurality of non-respiratory bodily actions of a plurality of persons, e.g. including the first person and a second person. Additionally or alternatively, determining 204 may be determining whether or not the plurality of persons are voluntarily attending on the non-respiratory bodily action at the present time. Determining 204 may be based on comparing 208 the plurality of non-respiratory bodily actions with the at least one predetermined threshold. Generating 206 feedback may comprise generating feedback to be perceived by the plurality of persons if each of the plurality of persons are voluntarily attending on the non-respiratory bodily action at the present time.

The first person and the second person may be located physically together. Alternatively, the first person and the second person may be located in different physically locations, e.g. in separate rooms.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Embodiments and aspects are disclosed in the following items:

Item 1. A method for eliciting relaxation response and cultivating attention, comprising:
  processing by signal processing mean, at least one real-time non-respiratory bodily action signal input of a person performing;
  determining, in response to constantly comparing said real-time non-respiratory bodily action signal input with at least one predetermined threshold, whether said person is voluntarily attending on said non-respiratory bodily action at this moment or not;
  generating feedback that can be immediately perceived by said person through at least one response system, if said person is voluntarily attending on said non-respiratory bodily action at this moment.

Item 2. The method of item 1, further comprising: reducing, adjusting said generated feedback, or stop generating feedback through said response system, as soon as said person is not voluntarily attending to said non-respiratory bodily action at this moment.

Item 3. The method of item 1, further comprising: monitoring the moment to moment said non-respiratory bodily action of said person, generating said real-time signal of said non-respiratory bodily action, and sending said real-time signal to said signal processing mean.

Item 4. The method of item 3, wherein monitoring the moment to moment said non-respiratory bodily action is provided by sensors such as motion sensors, touch sensors, pressure sensors, audio sensors or visual sensors, which is dedicated to detect and measure said person's said non-respiratory bodily action.

Item 5. The method of item 1, wherein said at least one response system includes for example audio, visual, tactile systems or other response systems.

Item 6. The method of item 1, wherein said generated feedback is configured to reflect said person is voluntarily attending to said non-respiratory bodily action at this moment, or motivate said person to keep voluntarily attending to said non-respiratory bodily action, wherein said generated feedback includes for example ambient visuals, lights, nature sounds, calm music, tactile feedbacks, game incentives, and social connections.

Item 7. The method of item 1, wherein said generated feedback is to trigger a product function.

Item 8. The method of item 1, wherein said at least one predetermined threshold is real-time velocity, including both linear velocity and angular velocity, of said non-respiratory bodily action:

a. if said real-time signal input represents said non-respiratory bodily action is moving with a real-time velocity below said predetermined real-time velocity threshold, said person is considered as voluntarily attending on said non-respiratory bodily action at this moment; or
  b. if said real-time signal input represents said non-respiratory bodily action is moving with a real-time velocity equal or above said predetermined real-time velocity threshold, said person is considered as not voluntarily attending on said non-respiratory bodily action at this moment; or
  c. if said real-time signal input represents said non-respiratory bodily action is not moving, said person is considered as not voluntarily attending on said non-respiratory bodily action at this moment;

Item 9. The method of item 1, wherein said at least one predetermined threshold is time duration used for said non-respiratory bodily action to complete, or travel a certain distance or angle:

a. if said real-time signal input of said non-respiratory bodily action represents a time duration to complete said non-respiratory bodily action, or travel said distance or angle, which is above said predetermined time duration threshold to complete said non-respiratory bodily action, or travel said distance or angle, said person is considered as voluntarily attending on said non-respiratory bodily action at this moment; or
  b. if said real-time signal input of said non-respiratory bodily action represents a time duration to complete said non-respiratory bodily action, or travel said distance or angle, which is equal or below said predetermined time duration threshold to complete said non-respiratory bodily action, or travel said distance or angle, said person is considered as not voluntarily attending on said non-respiratory bodily action at this moment Item 10. The method of item 9, further comprising: detecting the continuity of said non-respiratory bodily action:

a. if said real-time signal input represents said non-respiratory bodily action is moving, said person is considered as voluntarily attending on said non-respiratory bodily action at this moment; or
  b. if said real-time signal input represents said non-respiratory bodily action is not moving, said person is considered as not voluntarily attending on said non-respiratory bodily action at this moment.

Item 11. The method of item 8, 9, further comprising: if said non-respiratory bodily action is caressing, another predetermined threshold is pressure applied on the caressed surface:

a. if said real-time signal input of said caressing action represents a pressure below said predetermined pressure threshold, said person is considered as voluntarily attending on said caressing action at this moment; or
  b. if said real-time signal input of said caressing action represents a pressure equal or above said predetermined pressure threshold, said person is considered as not voluntarily attending on said caressing action at this moment; or
  c. if said real-time signal input represents said caressing action does not apply any pressure on said caressed surface, said person is considered as not voluntarily attending to said caressing action at this moment.

Item 12. The method of item 8, 9, further comprising: if said non-respiratory bodily action is repetitive, another predetermined threshold is time duration between previous repetition ended and starting a new repetition of said non-respiratory bodily action:
  a. if said real-time signal input of said non-respiratory bodily action represents a time duration between previous repetition ended and starting a new repetition, which is below said predetermined threshold of time duration between previous repetition ended and starting a new repetition, said person is considered as voluntarily attending on said non-respiratory bodily action at this moment; or
  b. if said real-time signal input of said non-respiratory bodily action represents a time duration between previous repetition ended and starting a new repetition, which is equal or above said predetermined threshold of time duration between previous repetition ended and starting a new repetition, said person is considered as not voluntarily attending on said non-respiratory bodily action at this moment.

Item 13. The method of item 8, 9, further comprising: another predetermined threshold is minimum time duration said person has been voluntarily attending to said non-respiratory bodily action, where said feedback is only generated if said person has been voluntarily attending on said non-respiratory bodily action longer than said predetermined minimum time duration threshold.

Item 14. The method of item 1, further comprising: generating feedback through at least one response system, if plurality of persons voluntarily attending to said non-respiratory bodily action together at this moment, thus said generated feedback motivates said plurality of persons to keep voluntarily attending to said non-respiratory bodily action as a social activity.

Item 15. The method of item 14, wherein said generated feedback is compound feedback, it can be a dynamic visual composition where each person of said plurality of persons represents a specific colour, visual patterns, or a dynamic sound composition where each person of said plurality of persons represents a specific sound or music instrument, or other dynamic response compositions.

Item 16. The method of item 14, wherein said plurality of persons consciously attending to said non-respiratory bodily action together can either be located physically together, or distributed elsewhere with everyone can immediately perceive said generated feedback.

Item 17. A method for eliciting relaxation response and cultivating attention, the method comprising:
  processing by a signal processing mean, at least one real-time non-respiratory bodily action signal input indicative of a non-respiratory bodily action of a first person;
  determining, in response to constantly and/or continuously comparing the real-time non-respiratory bodily action signal input with at least one predetermined threshold, whether or not the first person is voluntarily attending on the non-respiratory bodily action at the present time; and
  generating feedback to be perceived by the first person through at least one response system if the first person is voluntarily attending on the non-respiratory bodily action at the present time.

Item 18. Method according to item 17 further comprising reducing and/or adjusting the generated feedback if the first person is not voluntarily attending on the non-respiratory bodily action at the present time.

Item 19. Method according to item 17 or 18 further comprising stopping the generation of feedback if the first person is not voluntarily attending to the non-respiratory bodily action at the present time.

Item 20. Method according to any of the preceding items further comprising detecting the non-respiratory bodily action of the first person, generating the at least one real-time non-respiratory bodily action signal input indicative of the non-respiratory bodily action of the first person, and transmitting the at least one real-time non-respiratory bodily action signal input to the signal processing mean.

Item 21. Method according to any of the preceding items wherein the at least one real-time non-respiratory bodily action signal input is detected by one or more sensors.

Item 22. Method according to item 21, wherein the one or more sensors comprises one or more motion sensor(s), touch sensor(s), pressure sensor(s), audio sensor(s) and/or visual sensor(s).

Item 23. Method according to any of the preceding items, wherein the at least one response system comprises one or more audio system(s), one or more visual system(s), and/or one or more tactile system(s).

Item 24. Method according to any of the preceding items, wherein the generated feedback is configured to reflect that the first person is voluntarily attending to the non-respiratory bodily action at the present time, and/or motivate the first person to keep voluntarily attending to the non-respiratory bodily action.

Item 25. Method according to any of the preceding items, wherein the generated feedback comprises one or more of ambient visual(s), light(s), nature sound(s), calm music, tactile feedback(s), game incentive(s), and social connection(s).

Item 26. Method according to any of the preceding items, wherein the generated feedback comprises triggering of a product function, such as activation and/or deactivation of a product.

Item 27. Method according to any of the preceding items, wherein the at least one real-time non-respiratory bodily action signal input comprises a real-time velocity input indicative of a real time velocity, such as a linear velocity and/or an angular velocity, of the non-respiratory bodily action, and the at least one predetermined threshold comprises a predetermined real-time velocity threshold, such as a predetermined linear velocity threshold and/or a predetermined angular velocity threshold.

Item 28. Method according to item 27, wherein if the real-time velocity input is below the predetermined real-time velocity threshold, the first person is considered as voluntarily attending on the non-respiratory bodily action at the present time.

Item 29. Method according to items 27 or 28, wherein if the real-time velocity input is above the predetermined real-time velocity threshold, the first person is considered as not voluntarily attending on the non-respiratory bodily action at the present time.

Item 30. Method according to any of the preceding items, wherein if the at least one real-time non-respiratory bodily action signal input indicates that the non-respiratory bodily action does not comprises movement, the first person is considered as not voluntarily attending on the non-respiratory bodily action at the present time.

Item 31. Method according to any of the preceding items, wherein if the at least one real-time non-respiratory bodily action signal input indicates that the non-respiratory bodily action comprises movement, the first person is considered as voluntarily attending on the non-respiratory bodily action at the present time.

Item 32. Method according to any of the preceding items, wherein the at least one real-time non-respiratory bodily action signal input comprises a time duration input indicative of a time duration used for the non-respiratory bodily action to complete, or travel a certain distance or angle, and the at least one predetermined threshold comprises a predetermined time duration threshold.

Item 33. Method according to item 32, wherein if the time duration input is above the predetermined time duration threshold the first person is considered as voluntarily attending on the non-respiratory bodily action at the present time.

Item 34. Method according to item 32 or 33, wherein if the time duration input is equal to or below the predetermined time duration threshold the first person is considered as not voluntarily attending on the non-respiratory bodily action at the present time.

Item 35. Method according to any of the preceding items, wherein the at least one real-time non-respiratory bodily action signal input comprises a continuity input indicative of continuity of the non-respiratory bodily action.

Item 36. Method according to any of the preceding items, wherein the at least one real-time non-respiratory bodily action signal input comprises a pressure input indicative of pressure applied on a surface by the non-respiratory bodily action, and the at least one predetermined threshold comprises a predetermined pressure threshold.

Item 37. Method according to item 36, wherein if the pressure input is below the predetermined pressure threshold, the first person is considered as voluntarily attending on the non-respiratory bodily action at the present time.

Item 38. Method according to item 36 or 37, wherein if the pressure input is equal to or above the predetermined pressure threshold, the first person is considered as not voluntarily attending on the non-respiratory bodily action at the present time.

Item 39. Method according to any of the preceding items, wherein if the at least one real-time non-respiratory bodily action signal input indicates that the non-respiratory bodily action does not comprise applying any pressure on a surface, the first person is considered as not voluntarily attending to the non-respiratory bodily action at the present time.

Item 40. Method according to any of the preceding items, wherein the at least one real-time non-respiratory bodily action signal input comprises a repetitiveness input indicative of time duration between a first repetition ending and a second repetition starting of the non-respiratory bodily action, and the at least one predetermined threshold comprises a predetermined repetitiveness threshold.

Item 41. Method according to item 40, wherein if the repetitiveness input is below the predetermined repetitiveness threshold, the first person is considered as voluntarily attending on the non-respiratory bodily action at the present time.

Item 42. Method according to item 40 or 41, wherein if the repetitiveness input is equal to or above the predetermined repetitiveness threshold, the first person is considered as not voluntarily attending on the non-respiratory bodily action at the present time.

Item 43. Method according to any of the preceding items, the method further comprising determining an attendance time indicative a time duration that the first person has been voluntarily attending to the non-respiratory bodily action, and comparing the attendance time with a predetermined attendance time threshold, and wherein the feedback is only generated if the first person has been voluntarily attending on the non-respiratory bodily action for a time duration longer than the predetermined attendance time threshold.

Item 44. Method according to any of the preceding items, the method further comprising processing by the signal processing mean a plurality of at least one real-time non-respiratory bodily action signal input indicative of a non-respiratory bodily action of a plurality of persons including the first person and a second person; determining, in response to constantly comparing the plurality of real-time non-respiratory bodily action signal input with the at least one predetermined threshold, whether or not the plurality of persons are voluntarily attending on the non-respiratory bodily action at the present time, wherein generating feedback comprises generating feedback to be perceived by the plurality of persons through the at least one response system if the plurality of persons are all voluntarily attending on the non-respiratory bodily action at the present time.

Item 45. Method according to item 44, wherein the generated feedback comprises a compound feedback, such as a dynamic visual composition wherein each person of the plurality of persons represents a specific colour and/or a specific visual pattern, and/or such as a dynamic sound composition wherein each person of the plurality of persons represents a specific sound and/or music instrument.

Item 46. Method according to item 44 or 45, wherein the plurality of persons are located physically together, or are distributed elsewhere.

The invention claimed is:

1. A system for relaxation and cultivation of attention, the system comprising:

a detection unit configured for detecting a muscle movement of a non-respiratory bodily action of a first person and generating at least one real-time muscle movement non-respiratory bodily action signal input indicative of the muscle movement of the non-respiratory bodily action;

at least one response system for generating feedback to be perceived by the first person; and a processing unit connected to the detection unit and the at least one response system, the processing unit being configured to receive the at least one real-time muscle movement non-respiratory bodily action signal input, and determine, based on comparing the at least one real-time muscle movement non-respiratory bodily action signal input with at least one predetermined threshold, whether or not the first person is voluntarily attending on the muscle movement of the non-respiratory bodily action at a present time, wherein determining that the first person is voluntarily attending on the muscle movement of the non-respiratory bodily action at the present time requires that the muscle movement of the non-respiratory bodily action has one or more of: a velocity or an angular velocity below a predetermined velocity threshold and above a non-movement threshold; an acceleration or an angular acceleration below a predetermined acceleration threshold; a pressure below a predetermined pressure threshold and above a non-pressure threshold; and a repetitiveness parameter below a predetermined non-repetitiveness threshold; and wherein, in response to determining that the first person is voluntarily attending on the muscle movement of the non-respiratory bodily action at the present time, the processing unit is further configured to generate feedback for motivating the first person to continuously sustain voluntary attention to the muscle movement of the non-respiratory bodily action, wherein the feedback is generated through the at least one response system.

2. The system of claim 1 wherein the repetitiveness parameter is a time duration between a first repetition ending and a second repetition starting of the muscle movement of the non-respiratory bodily action.

3. The system of claim 1 wherein determining that the first person is voluntarily attending on the muscle movement of the non-respiratory bodily action requires that the muscle movement of the non-respiratory bodily action has a continuity parameter above a predetermined continuity threshold.

4. The system of claim 1 wherein the detection unit comprises one or more sensors, wherein the one or more sensors comprises one or more motion sensor, touch sensor, pressure sensor, audio sensor or visual sensor.

5. The system of claim 1, wherein the at least one response system comprises one or more audio system, visual system, tactile system, or fragrance system.

6. The system of claim 1, wherein the processing unit is further configured to:
determine an attendance time indicative of a time duration that the first person has been voluntarily attending to the muscle movement of the non-respiratory bodily action; and
compare the attendance time with a predetermined attendance time threshold,
wherein the feedback is only generated if the first person has been voluntarily attending on the muscle movement of the non-respiratory bodily action for a time duration longer than the predetermined attendance time threshold.

7. A method comprising:
detecting, using a processor of an electronic device, a muscle movement of a non-respiratory bodily action of a first person;
determining, using the processor and based on comparing the muscle movement of the non-respiratory bodily action of the first person with at least one predetermined threshold, whether or not the first person is voluntarily attending on the muscle movement of the non-respiratory bodily action at a present time; and
activating, using the processor, a response function if the first person is voluntarily attending on the muscle movement of the non-respiratory bodily action at the present time,
wherein determining that the first person is voluntarily attending on the muscle movement of the non-respiratory bodily action requires that the muscle movement of the non-respiratory bodily action has one or more of: a velocity or an angular velocity below a predetermined velocity threshold and above a non-movement threshold; an acceleration or angular acceleration below a predetermined acceleration threshold; a pressure below a predetermined pressure threshold and above a non-pressure threshold; and, a repetitiveness parameter below a predetermined non-repetitiveness; and wherein in response to determining that the first person is voluntarily attending on the muscle movement of the non-respiratory bodily action at the present time, the processor generates feedback for motivating the first person to continuously sustain voluntary attention to the muscle movement of the non-respiratory bodily action.

8. The method of claim 7, wherein the muscle movement of the non-respiratory bodily action comprises a touch gesture, and wherein detecting the non-respiratory bodily action of the first person comprises detecting the touch gesture on a touch sensitive surface.

9. The method of claim 8, wherein the response function is related to a position of the touch gesture on the touch sensitive surface.

10. The method of claim 7, comprising activating a standard response function using the processor if the first person is not voluntarily attending on the muscle movement of the non-respiratory bodily action at the present time, and wherein the response function is different from the standard response function.

11. The method of claim 7, further comprising:
determining, using the processor, an attendance time indicative of a time duration that the first person has been voluntarily attending to the muscle movement of the non-respiratory bodily action; and
comparing, using the processor, the attendance time with a predetermined attendance time threshold,
wherein the feedback is only generated if the first person has been voluntarily attending on the muscle movement of the non-respiratory bodily action for a time duration longer than the predetermined attendance time threshold.

12. A method for relaxation and cultivation of attention, the method comprising:
detecting, using a detecting unit operably coupled to a processor, a body movement of a first person;
determining, using the processor, whether or not the first person is voluntarily attending on the body movement at the present time by comparing the body movement of the first person with at least one predetermined threshold; and
generating feedback using the processor to be perceived by the first person through at least one response system if the first person is voluntarily attending on the body movement at a present time,
wherein determining that the first person is voluntarily attending on the body movement requires that the body movement has one or more of: a velocity or an angular velocity below a predetermined velocity threshold and above a non-movement threshold; an acceleration or an angular acceleration below a predetermined acceleration threshold; a pressure below a predetermined pressure threshold and above a non-pressure threshold; and, a repetitiveness parameter below a predetermined non-repetitiveness threshold.

* * * * *